United States Patent [19]
Jin et al.

[11] Patent Number: 5,945,431
[45] Date of Patent: Aug. 31, 1999

[54] CYTOMEGALOVIRUS INHIBITING COMPOUNDS

[75] Inventors: Haolun Jin, Pierrefonds; Laval C. Chan, Kirkland; Wei Wang, Pierrefonds; Tomislav Stefanac, Laval; Tarek S. Mansour, Montreal; Paul Nguyen-Ba, Laprairie; Jean-Francois Lavallee, Blainville; Guy Falardeau, Ste.-Dorothee, all of Canada

[73] Assignee: Biochem Therapeutics Incorporated, Quebec, Canada

[21] Appl. No.: 08/923,604

[22] Filed: Sep. 4, 1997

Related U.S. Application Data

[63] Continuation of application No. PCT/CA97/00182, Mar. 14, 1997.

[30] Foreign Application Priority Data

Mar. 15, 1996 [GB] United Kingdom ................ 9605437

[51] Int. Cl.$^6$ ............... A61K 31/435; C07D 471/04
[52] U.S. Cl. ............. 514/300; 514/215; 540/580; 546/113; 546/122; 546/123
[58] Field of Search ................ 546/122, 113, 546/123; 514/300, 215; 540/580

[56] References Cited

U.S. PATENT DOCUMENTS

| | | |
|---|---|---|
| 4,786,644 | 11/1988 | Glamkowski et al. ........... 514/312 |
| 4,959,363 | 9/1990 | Wentland ........................ 514/235.2 |

FOREIGN PATENT DOCUMENTS

| | | |
|---|---|---|
| 0 470 252 A1 | 2/1992 | European Pat. Off. . |
| 0 612 731 A1 | 9/1994 | European Pat. Off. . |
| 0646 598 A1 | 4/1995 | European Pat. Off. . |
| WO 93 04043 | 3/1993 | WIPO . |
| WO 94 04775 | 2/1997 | WIPO . |

OTHER PUBLICATIONS

Peakdale's Fine Chemicals, 1995 Collection, pp. 1–38.
Peakdale's Fine Chemicals, 1994 Collection, pp. 1–41.
Peakdale's Fine Chemicals: Chemical Family 122 (PFC's 798–803); Chemical Family 123 (PFC's 804–813); and Chemical Family 124 (PFC's 814–819), respectively (1996).

*Primary Examiner*—Bernard Dentz
*Attorney, Agent, or Firm*—Nixon & Vanderhye

[57] ABSTRACT

The present invention relates to heterocyclic compounds having antiviral activity. In particular, compounds of formula (I):

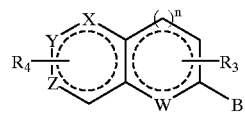

wherein B, W, X, Y, $R_1$, $R_2$, $R_3$, $R_4$ and n are as defined herein, are useful in the therapy and prophylaxis of cytomegalovirus (CMV) infection in mammals.

28 Claims, No Drawings

CYTOMEGALOVIRUS INHIBITING COMPOUNDS

This is a continuation of PCT application No. PCT/CA97/00182, filed 14 Mar. 1997.

FIELD OF THE INVENTION

The present invention relates to heterocyclic compounds, and more particularly, to naphthyridine compounds and their use in therapy and prophylaxis of cytomegalovirus (CMV) infection.

BACKGROUND OF THE INVENTION

Of the DNA viruses, the herpes group is the source of the most common viral illnesses in man. The group consists of herpes simplex virus (HSV) type I and II, varicella zoster (VZV) Epstein-Barr virus (EBV) and cytomegalovirus (CMV).

As with other herpes viruses, infection with CMV leads to a lifelong association of virus and host. Following a primary infection, virus may be shed for a number of years. Infection in otherwise healthy individuals is frequently asymptomatic, as 80% of the adult population harbor the virus in latent form. In immunocompromised individuals, such as chemotherapy patients, organ transplant patients and in particular AIDS sufferers, latent CMV can be re-activated resulting in microcephaly, hepatosplenomegaly, jaundice, convulsive seizures which may cause mental retardation, mononucleosis, retinitis and even death. In AIDS patients, CMV is a predominant cause of morbidity.

A variety of drugs have been developed to treat herpesvirus infection, including naturally occurring proteins and synthetic nucleoside analogs. For example, the natural antiviral protein, interferon, has been used in the treatment of herpesvirus infections, as have the nucleoside analogs, cytosine-arabinoside, adenine-arabinoside, iodoxyuridine and acyclovir, which is presently the treatment of choice for herpes simplex type I infection.

Unfortunately, drugs such as acyclovir that have proven effective to treat certain herpesviruses infections are not sufficiently effective of treat CMV. And, drugs currently used to treat CMV infection, such as ganiciclovir (9-[(1,3-dihyroxy-2-propoxy)methyl]guanine) and foscarnet (phosphonoformic acid), lack the acceptable side effect and safety profiles of the drugs approved for treatment of other herpesviruses.

Thus, there remains a need for therapeutic and prophylactic non-nucleoside agents effective to treat CMV infection. Accordingly, it is an object of the present invention to provide a method of inhibiting CMV replication in a mammal. It is also an object of the present invention to provide compounds and pharmaceutical compositions useful for inhibiting CMV replication in a mammal.

SUMMARY OF THE INVENTION

In one aspect, the present invention provides a method of inhibiting cytomegalovirus replication in a mammal comprising administering to said mammal an anti-cytomegaloviral amount of a compound of formula (I):

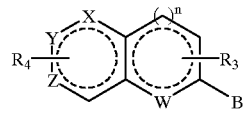
(I)

wherein
W is selected from CH, $CR_3$, $CH_2$, C=O, $CHR_3$, N and $NR_5$;
one of X, Y, and Z is N or $NR_5$ while the other two are independently selected from CH, $CR_4$, $CH_2$, C=O and $CHR_4$;
B is selected from the group consisting of;

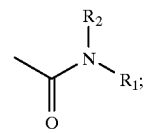
(II)

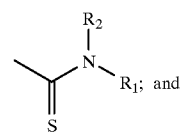
(III)

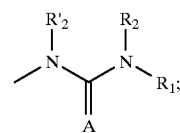
(IV)

wherein;
A is O or S;
$R_1$ Is selected from:
  $C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy,; and
  $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_2$ and $R'_2$ are independently H, $C_{1-4}$ alkyl or $R_1$ and $R_2$ together form a saturated or unsaturated 5 or 6 member heterocycle optionally fused to $C_{6-10}$ aryl or heteroaryl;
$R_3$ and $R_4$ are independently selected from H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo substituted $C_{1-4}$ alkyl or halo-substituted $C_{1-4}$ alkoxy, $C_{1-4}$ alkyl, $C_{1-4}$ alkoxy or carboxy;
$R_5$ is H, $C_{1-6}$ alkyl or $C_{1-6}$ acyl optionally substituted with OH, halogen, amino or $C_{1-4}$ alkoxy; and n is 0, 1 or 2.

In yet another aspect of the invention, there is provided cytomegalovirus inhibiting compounds and pharmaceutically acceptable salts thereof according to formula (I) provided that i) when A is

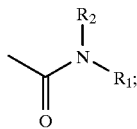
(II)

and when W and Y are both N or $NR_5$, then $R_1$ is other than allyl or 2-methoxybenzyl;

ii) when A is

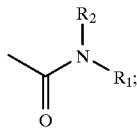
(II)

when either X or Z is N or $NR_5$, then W is N or $NR_5$; and ii) when A is

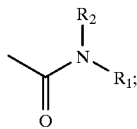
(II)

when Z is N or $NR_5$, then $R_1$ is other than methyl.

DETAILED DESCRIPTION OF THE INVENTION

In one aspect, the present invention provides a method of inhibiting cytomegalovirus replication in a mammal comprising administering to said mammal an anti-cytomegaloviral amount of a compound of formula (V):

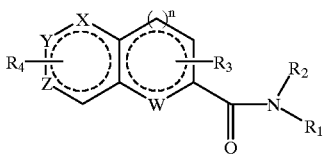
(V)

wherein

W is selected from CH, $CR_3$, $CH_2$, C=O, $CHR_3$, N and $NR_5$;

one of X, Y, and Z is N or $NR_5$ while the other two are independently selected from CH, $CR_4$, $CH_2$, C=O and $CHR_4$;

$R_1$ is selected from:

$C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl alkoxy, alkylthio, acyl, acyloxy or alkoxycarbonyl) optionally substituted with OH, halogen, amino or $C_{1-4}$ alkoxy; and $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;

$R_2$ is H, $C_{1-4}$ alkyl or $R_1$ and $R_2$ together form a saturated or unsaturated 5 or 6 member heterocycle optionally fused to $C_{6-10}$ aryl or heteroaryl;

$R_3$ and $R_4$ are independently selected from H, OH, halogen, amino, cyano and $C_{1-6}$ (alkyl, alkoxy, acyl acyloxy or alkoxycarbonyl) optionally substituted with OH, halogen, amino or $C_{1-4}$ alkoxy;

$R_5$ is H, $C_{1-6}$ alkyl or $C_{1-6}$ acyl optionally substituted with OH, halogen, amino or $C_{1-4}$ alkoxy; and n is 0, 1 or 2.

In an other aspect of the invention, there is provided a method of inhibiting cytomegalovirus replication in a mammal comprising administering to said mammal an anti-cytomegaloviral amount of a compound of formula (VI):

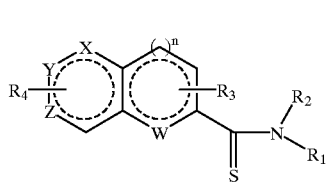
(VI)

wherein W, X, Y, Z, $R_1$ to $R_4$ and n are defined herein.

In an other aspect of the invention, there is provided a method of inhibiting cytomegalovirus replication in a mammal comprising administering to said mammal an anti-cytomegaloviral amount of a compound of formula (VII):

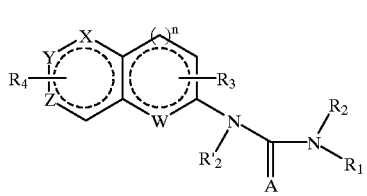
(VII)

wherein A is O or S and, W, X, Y, Z, $R_1$ to $R_4$ and n are defined herein.

In yet another aspect of the invention, there is provided cytomegalovirus inhibiting compounds and pharmaceutically acceptable salts thereof according to formula (I); (VI); (VI) or (VII).

In another aspect of the invention, there is provided anti-cytomegalovirus compositions comprising a pharmaceutically acceptable carrier, diluent or adjuvant and a compound of formula (I); (VI); (VI) or (VII) or a pharmaceutically acceptable salt thereof.

The present invention relates to compounds which inhibit CMV replication. These compounds are characterized by a heterobicyclic moiety as illustrated in formula (I), (V), (VI) or (VII):

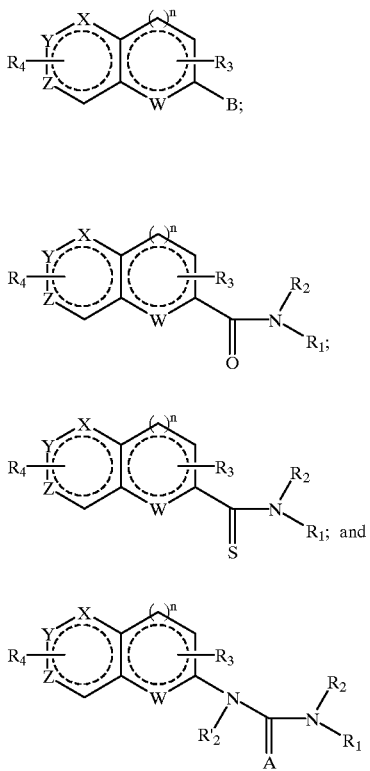

wherein A, B, W, X, Y, Z, $R_1$ to $R_4$ and n are defined herein.

The term "alkyl" as used throughout the specification refers to a saturated carbon chain which may be straight or branched. Similarly the term "alkenyl" is; a straight or branched carbon chain but incorporates unsaturated carbon atoms. For convenience however, the terms "alkoxy", "alkylthio", "acyl", "acyloxy" and "alkoxycarbonyl" refer to chains that are either saturated or unsaturated and may also be straight or branched. Where indicated, any of the above mentioned chains may have various substituents. It is understood that there may be one or more substituents unless otherwise specified.

The term "carbocycle" refers to a cyclic carbon chain or ring which is saturated or unsaturated. A "heterocycle" is a ring incorporating heteroatoms selected from N, O and S in place of carbon. Unsaturated carbocycles and heterocycles may be aromatic i.e. aryl such as phenyl or naphthyl, or heteroaryl such as pyridine or quinoline. Where indicated, any of the above mentioned rings may have various substitutions. It is understood that there may he one or more substituents unless otherwise specified.

The term "amino" includes primary amines i.e. $NH_2$, secondary amines i.e. NHR, or tertiary amines i.e. $N(R)_2$ wherein R is C1-4 alkyl. Also encompassed by the term are quaternary amines such as $NH_3^+$.

In methods of the present invention, cytomegalovirus replication is inhibited by administering compounds of formula (I), (V), (VI), and (VII) as shown above, wherein:

W is selected from CH, $CR_3$, $CH_2$, C=O, $CHR_3$, N and $NR_5$; and one of X, Y, and Z is N or $NR_5$ while the other two are independently selected from CH, $CR_4$, $CH_2$, C=O and $CHR_4$. It will be appreciated that the heterobicyclic compounds of the invention may be saturated, unsaturated or partially unsaturated and that W, X, Y and Z will have the appropriate valency for each condition. For example, when the rings are unsaturated, W may be N, CH or $CR_3$. And conversely, when the rings are saturated W may be $CH_2$, C=O, $CHR_3$, NH or NR,. The same principle applies for X, Y and Z.

In a preferred embodiment n is 1.

In a preferred embodiment W is N or $NR_5$;

In a preferred embodiment X is N or $NR_5$, while Y and Z are independently CH, $CR_4$, $CH_2$, C=O or $CHR_4$.

In a preferred embodiment Y is N or $NR_5$, while X and Z are independently CH, $CR_4$, $CH_2$, C=O or $CHR_4$.

In a preferred embodiment Z is N or $NR_5$, while X and Y are independently CH, $CR_4$, $CH_2$, C=O or $CHR_4$.

In a preferred embodiment the heterobicyclic ring incorporating W, X, Y and Z is unsaturated.

In a particularly preferred embodiment, W and Y are independently N or $NR_5$ while X and Z are independently CH, $CR_4$, $CH_2$, C=O or $CHR_4$.

In a particularly preferred embodiment, W and Y are both N while X and Z are CH or $CR_4$ and the heterobicyclic ring is unsaturated.

In a most preferred embodiment, W and Y are both N while X and Z are CH or $CR_4$, the heterobicyclic ring is unsaturated and n is 1, thereby forming a 1,6-naphthyridine ring.

In a preferred embodiment, A is O.

$R_1$ is selected from:

$C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy,; and $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy.

In a preferred embodiment $R_1$ is $C_{2-6}$ alkenyl; $C_{1-6}$ alkyl or $C_{3-7}$ cycloalkyl substituted with a 6 member aryl or heteroaryl or cycloalkyl ring optionally substituted with halogen, hydroxy, $C_{1-4}$ alkyl, $C_{1-4}$ alkoxy, $C_{1-4}$ alkylthio, $C_{1-4}$ alkoxycarbonyl, halo-substituted $C_{1-4}$ alkyl or halo-substituted $C_{1-4}$ alkoxy; and $C_{3-7}$ cycloalkyl fused to a 6 member aryl or heteroaryl ring optionally substituted with halogen, hydroxy, $C_{1-4}$ alkyl, $C_{1-4}$ alkoxy, $C_{1-4}$ alkylthio, $C_{1-4}$ alkoxycarbonyl or halo-substituted $C_{1-4}$ alkyl.

In a particularly preferred embodiment, $R_1$ is benzyl, pyridinylmethyl or cyclohexylmethyl optionally substituted with one or two substituents selected from hydroxy; amino, in particular $NH_2$ or $NH_3^+$; $C_{1-4}$ alkyl, in particular methyl; halogen, in particular fluoro, chloro or bromo; $C_{1-4}$ alkoxy, in particular methoxy or ethoxy; $C_{1-4}$ alkoxycarbonyl, in particular methoxycarbonyl; $C_{1-4}$ alkylthio, in particular methylthio; $C_{1-4}$ halo-substituted alkyl, in particular trifluoromethyl. More particularly preferred, $R_1$ is benzyl optionally mono or di-substituted at the 2, 3, 5 or 6 positions of the ring and most preferably at the 2 and/or 6 positions with methyl, methoxy, ethoxy, hydroxy, fluoro, bromo, chloro, methoxycarbonyl, methylthio, trifluoromethyl, trifluoromethoxy, $NH_2$ or $NH_3^+Cl^-$, In an ever more preferred embodiment, $R_1$ is benzyl optionally substituted at the 2-position with fluoro, chloro, bromo, methyl, methoxy, ethoxy, methoxycarbonyl, trifluoromethyl or $NH_3^+C^-$.

In another particularly preferred embodiment, $R_1$ is $C_{3-7}$ cycloalkyl substituted with phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl. More particularly preferred, the $C_{3-7}$ cycloalkyl is cyclopropyl.

In another particularly preferred embodiment, $R_1$ is $C_{3-7}$ cycloalkyl fused to phenyl which is optionally substituted with one or two substituents selected from hydroxy, amino, $C_{1-4}$ alkyl, halogen, $C_{1-4}$ alkoxy, $C_{1-4}$ alkoxycarbonyl, $C_{1-4}$ alkylthio or $C_{1-4}$ halo-substituted alkyl. More particularly preferred, the $C_{3-7}$ cycloalkyl is cyclopentyl or cyclohexyl.

$R_2$ and $R'_2$ are independently H, $C_{1-4}$ alkyl or $R_1$ and $R_2$ together form a saturated or unsaturated 5 or 6 member heterocycle optionally fused to $C_{6-10}$ aryl or heteroaryl. In a preferred embodiment $R_2$ is H or methyl and most preferably H. $R'_2$ is H or methyl and most preferably H In another preferred embodiment $R_2$ together with $R_1$ form a saturated or unsaturated 5 or 6 member heterocycle optionally fused to $C_{6-10}$ aryl or heteroaryl. Suitable 5 or 6 member heterocycles include piperidine, piperazine, morpholine, pyrrole, pyrazole and imidazole. These may be fused to a $C_{6-10}$ aryl or heteroaryl to give suitable bicyclic rings such as indole, purine, benzimidazole, quinoline or isoquinoline.

$R_3$ and $R_4$ are independently selected from H, OH, halogen, amino, cyano and $C_{1-6}$ (alkyl, alkoxy, acyl, acyloxy and alkoxycarbonyl) optionally substituted with OH, halogen, amino or $C_{1-4}$ alkoxy It is appreciated that the ring incorporating X, Y and Z, may be substituted with one to four substituents $R_4$ while the ring incorporating W may be substituted with one to three substituents $R_3$.

$R_3$ and $R_4$ are independently saturated or unsaturated $C_{2-10}$ (carbocycle or heterocycle) optionally substituted with OH, halogen, amino, mercapto, $C_{1-4}$ alkyl, $C_{1-4}$ alkoxy or carboxy;

In an alternative embodiment, $R_3$ and $R_4$ are independently 6 member aryl or heteroaryl or cycloalkyl ring optionally substituted with halogen, hydroxy, $C_{1-4}$ alkyl, $C_{1-4}$ alkoxy.

In an alternative embodiment, $R_4$ is a 6 member aryl or heteroaryl or cycloalkyl ring optionally substituted with halogen, hydroxy, $C_{1-4}$ alkyl, $C_{1-4}$ alkoxy. In a further embodiment, $R_4$ is a 6 membered heteroaryl. In a further embodiment, $R_4$ is pyridyl.

In a preferred embodiment, there is one $R_3$ substituent which is selected from H; OH; halogen, in particular fluoro or chloro; and $C_{1-4}$ alkoxy, in particular methoxy or ethoxy. More preferably, $R_3$ is H, chloro, hydroxy or methoxy and most preferably H.

In a preferred embodiment, $R_4$ is selected from H, halogen, amino, OH, $C_{1-6}$ (alkyl, alkoxy, acyl, acyloxy and alkoxycarbonyl) optionally substituted with OH, halogen or amino. Preferably, there is one or two $R_4$ substituents and most preferably there is one $R_4$ substituent.

In a more preferred embodiment $R_4$ is amino.
In a more preferred embodiment $R_4$ is $C_{1-4}$ aminoalkyl.
In a more preferred embodiment $R_4$ is OH.
In a more preferred embodiment $R_4$ is halogen.
In a more preferred embodiment $R_4$ is methoxy.
In a most preferred embodiment $R_4$ is i.

$R_5$ is H, C, alkyl or acyl optionally substituted with OH, halogen, amino or $C_{1-4}$ alkoxy.

In a preferred embodiment $R_5$ is H.
In a preferred embodiment $R_5$ is $C_{1-4}$ alkyl and more preferably methyl.
In a preferred embodiment $R_5$ is $C_{1-4}$ alkyl substituted with amino and more preferably methyl or ethyl substituted with $NH_2$.

In a preferred embodiment $R_5$ is $C_{1-4}$ acyl and more preferably ethanoyl.
In a preferred embodiment $R_5$ is $C_{1-4}$ acyl substituted with amino and more preferably ethanoyl substituted with $NH_2$.

Preferred compounds of the invention include:
compound #1 N-(2-methylbenzyl)-2-(1,6)naphthyridinecarboxamide;
compound #2 N-benzyl-2-(1,6)naphthyridinecarboxamide;
compound #3 N-(4-bromobenzyl)-2-[1,6]naphthyridinecarboxamide
compound #4 N-(2-chlorobenzyl)-2-(1,6)naphthyridinecarboxamide;
compound #5 N-(2-bromobenzyl)-2-(1,6)naphthyridinecarboxamide;
compound #6 N-(3-bromobenzyl)-2-(1,6)naphthyridinecarboxamide;
compound #7 N-(2-fluorobenzyl)-2-(1,6)naphthyridinecarboxamide;
Compound #8 N-(4-chlorobenzyl)-2-[1,6]napthyridinecarboxamide
compound #9 N-(2-ethyloxybenzyl)-2-(1,6)naphthyridinecarboxamide;
compound #10 [1,6]naphthyridine-2-carboxylic acid indan-1-ylamide
compound #11 [1,6]naphthyridine-2-carboxylic acid (1,2,3,4-tetrahydro-naphthalen-1-yl)-amide
compound #12 N-(3-methoxybenzyl)-2-(1,6)naphthyridinecarboxamide;
compound #13 N-(2-trifluoromethylbenzyl)-2-(1,6)naphthyridinecarboxamide;
compound #14 N-(2,6-dimethoxybenzyl)-2-(1,6)naphthyridinecarboxamide;
compound #15 [1,6]naphthyridine-2-carboxylic acid (trans-2-phenyl-cyclopropyl)-amide
compound #16 N-(2-amino-6-fluorobenzy)-2-[1,6]naphthyridinecarboxamide
compound #17 [1,6]naphthyridine-2-carboxylic acid (1-phenyl-ethyl) amide;
compound #18 [1,6]naphthyridine-2-carboxylic acid (pyridine-2-ylmethyl) amide
compound #19 [1,6]naphthyridine-2-carboxylic acid cyclohexyl-methylamide
compound #20 (3,4-dihydro-1h-isoquinolin-2-yl)-[1,6]naphthyridin-2-yl-methanone
compound #21 N-(2-methylthiobenzyl)-2-[1,6]naphthyridine carboxamide
compound #22 N-(2-hydroxybenzyl)-2-(1,6)naphthyridinecarboxamide;
compound #23 N-(2-methoxycarbonylbenzyl)-2-(1,6)naphthyridine carboxamide;
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;
compound #27 (2-{([1,6]naphthyridine-2-carbonyl)-amino]-methyl}-phenyl)-carbonic acid tert-butyl ester;
compound #28 [1,6]Naphthyridine-2-carboxylic acid (2,3,4,5-tetrahydrobenzo[B]oxepin-5-yl)-amide
compound #29 [1,6]Naphthyridine-2-carboxylic acid (chroman-4-yl)-amide;
compound #30 N-(2'-methoxybenzyl)-5-amino-2-[1,6]naphthyridinecarboxamide;
compound #31 [1,6]Naphthyridine-2-carboxylic acid 2,3-(methylenedioxy)-benzylamide;

compound #32 7,8-dihydroisoquinolin-6-carboxylic acid 2'-methoxybenzylamide;
compound #33 8-bromo-[1,6]naphthyridine-2-carboxylic acid (2-N-ethylaminobenzylamide);
compound #34 8-bromo-[1,6]naphthyridine-2-carboxylic acid (2-isopropoxybenzylamide);
compound #35 8-bromo- [1,6)naphthyridine-2-carboxylic acid (2-methoxybenzylamide);
compound #36 8-chloro-1,6]naphthyridine-2-carboxylic acid (2-isopropoxybenzylamide);
compound #37 8-chloro-[1,6]naphthyridine-2-carboxylic acid (2-N-ethylaminobenzylamide);
compound #38 8-(2pyridyl)-[1,6]naphthyridine-2-carboxylic acid (2--isopropoxybenzylamide);
compound #39 [1,6]Naphthyridine-2-thiocarboxylic acid-2-trifluoromethylbenzylamide
compound #40 [1,6]Naphthyridine-2-thiocarboxylic acid-2-isopropoxybenzylamide;
compound #41 [1,6]Naphthyridine-2-thiocarboxylic acid-3-methoxybenzylamide;
compound #42 8-bromo-[1,6]Naphthyridine-2-thiocarboxylic acid-2-isopropoxybenzylamide;
compound #43 [1,6]Naphthyridine-2-thiocarboxylic acid 2-methoxy-benzylamide;
compound #44 [1,6]Naphthyridine-2-thiocarboxylic acid 2-ethoxy-benzylamide;
compound #45 [1,6]Naphthyridine-2-thiocarboxylic acid-2-methoxy-cyclohexylmethyl-amide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea;
compound #48 1-(N-boc-4-aminobutyl)-3-[1,6]naphthyridin-2-yl-urea;
compound #49 1-(4-aminobutyl)-3-[1,6]naphthyridin-2-yl-urea hydrochloride;
compound #50 1-[(S)-α-methylbenzyl]-3-[1,6]naphthyridin-2-yl-urea;
compound #51 1-[(R)-α-methylbenzyl]-3-[1,6]naphthyridin2-yl-urea;
compound #52 1-(2-methoxy-phenyl)-3-[1,6]naphthyridin-2yl-urea;
compound #53 1-butyl-3-[1,6]naphthyridin-2-yl-urea;
compound #54 1-(2-methoxybenzyl)-3-[1,6]naphthyridin-2-yl-urea;
compound #55 1-(2-ethoxy-phenyl)-3-[1,6]naphthyridin-2-yl-urea;
Compound #56 1-(2-methyl-phenyl)-3-[1,6]naphthyridin-2-yl-urea; and
Compound #57 8-(2-pyridyl)-[1,6]naphthyridine-2-carboxylic acid (2-isopropoxybenzylamide).

More Preferred compounds of this invention include:
compound #2 N-benzyl-2-(1,6)naphthyridinecarboxamide;
compound #4 N-(2-chlorobenzyl)-2-(1,6)naphthyridinecarboxamide;
compound #12 N-(3-methoxybenzyl)-2-(1,6)naphthyridinecarboxamide;
compound #14 N-(2,6-dimethoxybenzyl)-2-(1,6)naphthyridinecarboxamide;
compound #19 [1,6]naphthyridine-2-carboxylic acid cyclohexyl-methylamide
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;

compound #28 [1,6]Naphthyridine-2-carboxylic acid (2,3,4,5-tetrahydrobenzo[B]oxepin-5-yl)-amide;
compound #31 [1,6]Naphthyridine-2-carboxylic acid 2,3-(methylenedioxy)-benzylamide;
compound #32 7,8-dihydroisoquinolin-6-carboxylic acid 2'-methoxybenzylamide;
compound #33 8-bromo-[1,6naphthyridine-2-carboxylic acid (2-N-ethylaminobenzylamide);
compound #35 8 bromo-[1,6]naphthyridine-2-carboxylic acid (2-methoxybenzylamide);
compound #36 8-chloro-[1,6]naphthyridine-2-carboxylic acid (2-isopropoxybenzylamide);
compound #40 [1,6]Naphthyridine-2-thiocarboxylic acid-2-isopropoxybenzylamide;
compound #43 [1,6]Naphthyridine-2-thiocarboxylic acid 2-methoxy-benzylamide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea; and
compound #51 1-[(R)-α-methylbenzyl]-3-[1,6]naphthyridin-2-yl-urea.

Most Preferred compounds of this invention include:
compound #26 N-(2-propoxybenzyl)-2-[1,6]naphthyridine-2-carboxamide;
compound #32 7,8-dihydroisoquinolin 6-carboxylic acid 2'-methoxybenzylamide;
compound #33 8-bromo-[1,6]naphthyridine-2-carboxylic acid (2-N-ethylaminobenzylamide);
compound #36 8-chloro-[1,6]naphthyridine-2-carboxylic acid (2-isopropoxybenzylamide)
compound #40 [1,6]Naphthyridine-2-thiocarboxylic acid-2-isopropoxybenzylamide;
compound #43 [1,6]Naphthyridine-2-thiocarboxylic acid 2-methoxy-benzylamide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea; and
compound #51 1-[(R)-(-methylbenzyl]-3-[1,6]naphthyridin-2-yl-urea.

In a further preferred embodiment, the compounds of this invention include:
compound #26 N-(2propoxybenzyl)-2-[1,6]naphthyridine-2-carboxamide;
compound #32 7,8-dihydroisoquinolin-6-carboxylic acid 2'-methoxybenzylamide;
compound #33 8-bromo-[1,6]naphthyridine-2-carboxylic acid (2-N-ethylaminobenzylamine;
compound #40 [1,6]Naphthyridine-2-thiocarboxylic acid-2-isopropoxybenzylamide; and
compound #46 1-(2-iso-propoxy-phenyl)-3-[1,6]naphthyridin-2-yl-urea.

Compounds of the present invention can be synthesized using conventional preparative steps and recovery methods known to those skilled in the art of organic chemistry. A preferred synthetic route for producing compounds of formula V. involves coupling a carboxylic acid intermediate of formula a with an amino intermediate of formula b. The reaction will be under suitable conditions for amide bond formation i.e. in the presence of a suitable coupling agent such as EDC or dCC, to yield final compound of formula V. The reaction is illustrated in scheme 1. Compounds of formula V can be converted to compounds of formula VI by reacting them with thionation agents such as Lawesson's reagent. The use of Lawesson's reagent is well known in the art (for example, see *Synthesis,* 941 (1979); *Tetrahedron,* 35, 2433 (1979); and *Tet. Lett.,* 21, 4061 (1980).

A preferred synthetic route for producing bicyclic compounds of formula VI involved coupling a bicyclic amino intermediate of formula c with an amido moiety d. This reaction is illustrated by scheme 2. The reaction will be under suitable condition for <<urea>> bond formation, ip. appropriate solvent to yield to compounds of formula VIIa. Introduction of an $R_2$ substituent on the nitrogen can be done using method known in the art. The urea bond of compounds VIIa and VIIb can also be converted to a thiourea by reacting the compounds with thionation agents as mentioned above.

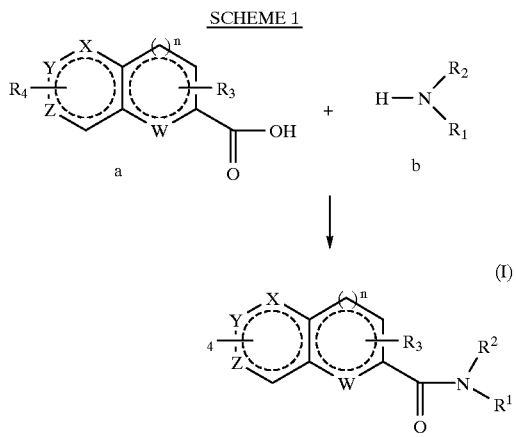

wherein X, Y, Z, $R_1$ to $R_4$ and n are as previously defined.

Intermediates a, b and c may be obtained from commercial sources, for instance, 2-carboxy-[1,6]naphthyridine (Peakdale Fine Chemicals, Glossop, Derbyshire UK, PFC-027); 6,7-dibromo-4-hydroxy-[1,5]naphthyridine-2-carboxylic acid (Pomorski et al Rocz. Chem., 1974, 48(2):321); 1,2,3,4-tetrahydro-8-hydroxy-[1,6]naphthyridine-2-carboxylic acid (Abe et al Tet. Lett., 1977, 9:735). Or, alternatively intermediates a, b and c may be prepared according to established synthetic techniques.

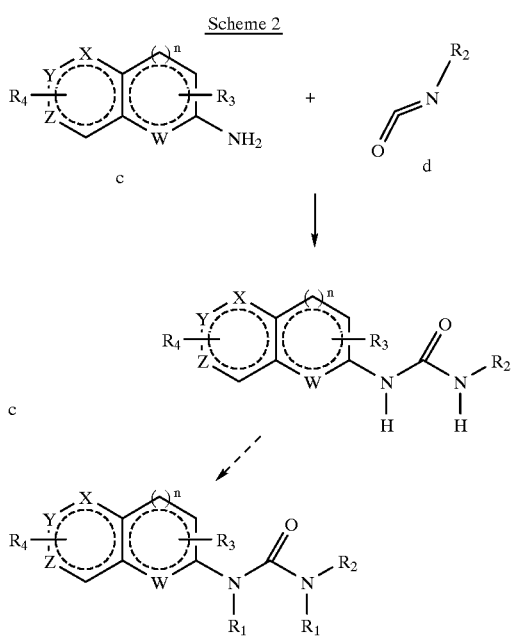

It will be appreciated that certain substituents require protection during the course of the synthesis and subsequent deprotection. For example, when $R_3$ or $R_4$ is hydroxyl, it may be necessary to protect it by converion to an alkoxy or an ester and subsequently deprotected. Protective groups for other substituents aye described in *Protective Groups in Organic Synthesis*, 2nd ed., Greene and Wuts, John Wiley & Sons, New York, 1991.

It will be appreciated by those skilled in the art that the compounds of formula I, V, VI and VII, de(pending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

The present invention also provides anti-cytomegalovirus compositions which comprise a pharmaceutically acceptable carrier or adjuvant and an amount of a compound of formula I, V, VI and VII effective to inhibit CMV replication in a mammal. The proportion of each carrier, diluent or adjuvant is determined by the solubility and chemical nature of the compound and the route of administration according to standard pharmaceutical practice.

Therapeutic and prophylactic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions. Compounds of the invention may also be administered via an intraocular implant for treating retinitis as a result of CMV infection. In particular, compounds may be embedded in a polymer based implant which will be release into the eye over an extended period of time.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrrolidone; fillers, such as lactose, sugar, maize-starch, calcium phosphate, sorbitol or glycine; tableting lubricants such as magnesium stearate; disintegrants, such as search, polyvinylpyrolidone, sodium starch glycoallate or microcryystalle cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 1 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting, or the like. Repeated blending operations may be used to distribute the active agent throughout those compositions employing large quantities of tillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. adjuvants, such as a local anesthetic a preservative or a buffering agent, may be dissolved in the vehicle prior to use. Stability of the pharmaceutical composition may be enhanced by freezing the composition after filling the vial and removing the water under vacuum, (E.g., freeze drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a cytomegalovirus replication inhibiting amount of a compounds of formula I, V, VI and VII and a pharmaceutically acceptable carrier, diluent or adjuvant. Typically, they contain from about 0.1% to about 99% by weight of active compound, and preferably from about 10% to about 60% by weight depending on which met-hod of administration is employed.

A cytomegalovirus replication inhibiting amount is that amount of active compound required to slow the progression of viral replication or reduce viral load from that which would otherwise occur without administration of said compound. Or, it is an amount of active compound required to slow the progression or reduce the intensity of symptoms resulting from CMV infection or elimination thereof.

Cytomegalovirus inhibiting activity of compounds of the invention can be determined according to the plaque reduction assay described in detail in the examples. Under these particular conditions, a compound having such activity will exhibit an $IC_{50}$ of approximately 50 $\mu$g/ml or less, preferably 25 $\mu$g/ml or less, more preferably 10 $\mu$g/ml or less, and most preferably less than 1 $\mu$g/ml.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

To further assist in understanding the present invention, the following non-limiting examples are provided.

EXAMPLE I

Synthesis compound #1 N-(2-methylbenzyl)-2-[1,6] naphthyridinecarboxamide

To a stirring mixture of 2-[1,6]naphthyridinecarboxylic acid (50 mg, 0.287 mmol), in anhy. THF (5 ml) at 0° C. was added triethylamine (44 ml, 0.316 mmol). After 5 min, isopropylchloroformate (0.316 ml, 1M solution in toluene, 0.316 mmol) was added. The mixture was stirred at 0° C. for 20 min. then 2-methylbenzylamine (53.46 ml, 0.43 mmol) was added to the mixture at 0° C. The resulting mixture was allowed to warm to room temperature and stirred at room temperature for 5h then diluted in $CH_2Cl_2$ (100 ml). The organic layer was washed with water, dried over anhy. $MgSO_4$, and concentrated to give the crude mixture. Chromatography of the crude (Hex:E:tOAc=1:1 to pure EtOAc) afforded desired product as white solid (29.8 mg, 37%): m.p. 120–121° C.

compound #2 N-benzyl-2-[1,6] naphthyridinecarboxamide To a stirring mixture of 2-[1,6] naphthyridinecarboxylic acid (50 mg, 0.287 mmol), 1-hydroxybenzo-triazole hydrate (42.7 mg, 0.316 mmol), benzylamine (45 mg, 0.42 mmol) in anhy. THF (5 ml) at 0° C. was added 1-(3-dimethylaminopropyl)-3-ethylcarbodiimide hydrochloride (60.6 mg, 0.316 mmol). The resulting mixture was allowed to stir at RT. After 20 min, DMF (2 ml) was added to the reaction mixture and the mixture was allowed to stir at room temperature overnight and it was found to be clear. The solvent was removed under vacuum and the resulting residue was redissolved in $CH_2Cl_2$ (100 ml). The organic layer was washed with aq. $NaHCO_3$, dried over anhy. $MgSO_4$, and concentrated to give the crude mixture. Chromatography of the crude (Hex: EtOAc=1:1 to pure EtOAc) afforded desired product as white solid (97 mg, 99%): m.p. 113–115° C.

compound #3 N (4-bromobenzyl)-2-[1,6] naphthyridinecarboxamide

To a stirring solution of 4-bromobenzylamine hydrochloride (97.8 mg, 98%, 0.43] mmol) in anhy. DMF (5 ml) was added triethylamine (60.1 ul. 0.431 mmol), After 5 min, 2-[1,6]naphthyridinecarboxylic acid (50 mg, 0.287 mmol), 1-hydroxybenzotriazole hydrate (42.7 mg, 0.316 mmol) and 1-(3-dimethylamino-propyl)-3-ethylcarbodiimide hydrochloride (60.6 mg, 0.316 mmol) was sequentially added. The resulting mixture was allowed to stir at room temperature for overnight and it was found to be clear. The solvent was removed under vacuum and the resulting residue was redissolved in $CH_2Cl_2$ (100 ml). The resulting mixture was allowed to stir at room temperature overnight and it was found to be clear. The solvent was removed under vacuum and the resulting residue was redissolved in $CH_2Cl_2$ (100 ml). The organic layer was washed with aq. $NaHCO_3$, dried over anhy. $MgSO_4$, and concentrated to give the crude mixture. Chromatography of the crude (Hex:EtOAc =1:1 to pure EtOAc) afforded desired product as white solid (97 mg, 99 m.p. 149–150° C.

compound #4 N-(2-chlorobenzyl)-2-[1,6] naphthyridinecarboxamide

To a stirring mixture of 2-[1,6]naphthyridinecarboxylic acid (50 mg, 0.287 mmol) in anhy. DMF (5 ml) at room temperature was sequentially added 1-hydroxybenzotriazole hydrate (42.7 mg, 0.316 mmol), 2-chlorobenzylamine (54.7 μl, 95%., 0.43 mmol) and 1-(3-dimethylaminopropyl)-3-ethylcarbodiimide hydrochloride (60.6 mg, 0.316 mmol). The resulting mixture was allowed to stir at room temperature overnight and it was found to be clear. The solvent was removed under vacuum and the resulting residue was redissolved in $CH_2Cl_2$ (100 ml). The resulting mixture was allowed to stir at room temperature overnight and it was found to be clear. The solvent was removed under vacuum and the resulting residue was redissolved in $CH_2Cl_2$ (100 ml). The organic layer was washed with aq. $Na(CO_3)$, dried over anhy. $MgSO_4$, and concentrated to give the crude mixture. Chromatography of the crude (Hex: EtOAc=1:1 to pure EtOAc) afforded desired product as white solid (83 mg, 97%): m.p. 120–121° C.

compound #5 N-(2-bromobenzyl)-2-[1,6]naphthyridine-carboxamide

To a stirring solution of 2-bromobenzylamine hydrochloride (80.7 mg, 95%, 0.345 mmol) in anhy. DMF (5 ml) was added triethylamine (51.8 ul. 0.345 mmol). After 5 min, 2-[1,6]naphthyridinecarboxylic acid (40 mg, 0.229 mmol), 1-hydroxybenzotriazole hydrate (34.2 mg, 0.253 mmol) and 1-(3-dimethylamino-propyl)-3-ethylcarbodiimide hydrochloride (48.5 mg, 0.253 mmol) was sequentially added. The resulting mixture was allowed to stir at room temperature for 4 h and it was found to be clear. The solvent was removed under vacuum and the resulting residue was redissolved in $CH_2Cl_2$ (100 ml). The organic layer was washed with aq. $NaHCO_3$, dried over anhy. $MgSO_4$, and concentrated to give the crude mixture Chromatography of the crude (Hex:EtOAc=1:1, pure EtOAc) afforded desired product as white solid (70 mg, 89% 129–130° C.

compound #6 N-(3-bromobenzyl)-2-[1,6] naphthyridinecarboxamide

To a stirring solution of 3-bromobenzylamine hydrochloride (77.5 mg, 0.345 mmol) in anhy. DMF (5 ml) was added triethylamine (51.8 ul. 0.345 mmol.), After 5 min, 2-[1,6]naphthyridinecarboxylic acid (40 mg, 0.229 mmol), 1-hydroxybenzotriazole hydrate (34.2 mg, 0.253 mmol) and 1-(3-dimethylamino-propyl)-3-ethylcarbodiimide hydrochloride (48.5 mg, 0.253 mmol) was sequentially added. The resulting mixture was allowed to stir at room temperature overnight and it was found to be clear. The solvent was removed under vacuum and the resulting residue was redissolved in $CH_2Cl_2$ (100 ml). The organic layer was washed with aq. $NaHCO_3$, dried over anhy. $MgSO_4$, and concentrated to give the crude mixture. Chromatography of the crude (Hex:EtOAc=1:1 to pure EtOAc) afforded desired product as white solid (64 mg, 81%): m.p. 112–113° C.

compound #7 N-(2-fluorobenzyl)-2-[1,6] naphthyridinecarboxamide

To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 2-fluorobenzyl amine (51.0 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was redissolved in $CH_2Cl_2$ (50 mL). The organic layer was washed with aq. $NaHCO_3$, dried over anhydrous $Na_2SO_4$ and concentrated to give the crude mixture. Flash column chromatography of the crude (50% hexane/ethyl acetate to 100% ethyl acetate) afforded the desired product as a white solid (79.2 mg, 98%) m.p. 110–111° C.

compound #8 N-(4-chlorobenzyl)-2-[1,6] naphthyridinecarboxamide

To a stirring mixture of 2-[1,6]naphthyridinecarboxylic acid (50 mg, 0.287 mmol) in anhydrous DMF (6.3 mL) at room temperature was added sequentially -hydroxybenzotriazole hydrate (42.7 mg, 0.316 mmol), 4-chlorobenzyl amine (53.5 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was redissolved in $CH_2Cl_2$ (50 mL). The organic layer was washed with aq. $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (80.3 mg, 94%): m.p. 110–111° C.

compound #9 N-(2-ethoxybenzyl)-2-[1,6] naphthyridinecarboxamide

To a stirring mixture of 2-[1,6]naphthyridinecarboxylic acid (50 mg, 0.287 mmol) in anhydrous DMF (6.3 mL) at room temperature was added sequentially 1 hydroxybenzotriazole hydrate (42.7 mg, 0.316 mmol), 2-ethoxybenzyl amine (64.9 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was redissolved in $CH_2Cl_2$ (50 mL). The organic layer was washed with aq. $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (85.0 mg, 96%): m.p. 79–80° C.

compound #10 [1,6]naphthyridine-2-carboxylic acid indan-1-ylamide

To a stirring mixture of 2-[1,6]naphthyridinecarboxylic acid (50 mg, 0.287 mmol) in anhydrous DMF (6.3 mL) at room temperature was added sequentially 1-hydroxybenzotriazole hydrate (42.7 mg, 0.316 mmol), 1-aminoindan (56.0 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was redissolved in $CH_2Cl_2$ (50 mL). The organic layer was washed with aq. $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (80.1 mg, 96%): m.p. 156–157° C.

compound #11 [1,6]naphthyridine-2-carboxylic acid (1,2,3,4-tetrahydro-naphthalen-1-yl)-amide To a stirring mixture of 2-[1,6]naphthyridinecarboxylic acid (50 mg, 0.287 mmol) in anhydrous DMF (6.3 mL) at room -temperature was added sequentially 1-hydroxybenzotriazole hydrate (42.7 mg, 0.316 mmol), 1,2,3,4-tetrahydro-1-naphthylamine (63.0 μL, 0.431 mmol) and 1-(3dimethylaminopropyl)-3-ethylcarboiimide hydrochloride (61.8 mg, 0.316 mmol). The resulting mixture was allowed to stir at room temperature overnight and it was found to be clear. The solvent was removed under vacuum and the resulting residue was re-dissolved in $CH_2Cl_2$ (50 mL). The organic layer was washed with aq. $NaHCO_3$, dried over anhydrous $Na_2SO_4$, and concentrated to give the crude mixture. Flash column chromatography of the crude (50% hexane/ethyl acetate to 100% ethyl acetate) afforded the desired product as a white solid (87.0 mg, 100%): m.p. 164–165° C.

compound #12 N-(3-methoxybenzyl)-2-[1,6] naphthyridinecarboxamide

To a stirring mixture of 2-[1,6]naphthyridinecarboxylic acid (50 mg, 0.287 mmol) in anhydrous DMF (10 mL) at room temperature was added sequentially 1-hydroxybenzotriazole hydrate (42.7 mg, 0.316 mmol), 3-methoxybenzylamine (56.6 μL, 0.431 mmol) and 1-(3-dimethylaminopropyl-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a clear oil (79.1 mg, 94%).

compound #13 N-(2-trifluoromethylbenzyl)-2-[1,6] naphthyridinecarboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-(trifluoromethyl)benzylamine (61.6 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (90.9 mg, 96%): m.p. 125–127° C.

compound #14 N-(2, 6-dimethoxybenzyl)-2-[1,6] naphthyridinecarboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2, 6-dimethoxybenzylamine (75.0 mg, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl restate to 100 ethyl acetate) afforded the desired product as a white solid (90.6 mg, 98%): m.p. 169°–171° C.

compound #15 [1,6]naphthyridine-2-carboxylic acid (trans-2-phenyl-cyclopropyl)-amide To a stirring mixture of trans-2-phenylcyclopropylamine hydrochloride (75.3 mg, 0.431) in anhydrous DMF (1.0 mL) was added triethylamine (60.0 μL, 0.431 mmol). After 5 minutes, 2-[1,6]naphthyridinecarboxylic acid (50 mg, 0.287 mmol), 1-hydroxybenzotriazole hydrate (42.7 mg, 0.316 mmol), and 1-(3-dimethylaminopropyl)-3-ethylcarboiimide hydrochloride (61.8 mg, 0.316 mmol) were added sequentially. The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (79.2 mg, 95 m) m.p. 123–124° C.

compound #16 N-(2-amino-6-fluorobenzyl)-2-[1,6] naphthyridinecarboxamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-amino-6-fluorobenzylamine (60.0 μL) and 1-(3-dimethylaminopropyl)-3-ethylcarboiimide hydrochloride (61.8 mg, 0.316 mmol) The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a white solid (80.0 mg, 94%): m.p. 165 (dec.).

compound #17 [1,6]naphthyridine-2-carboxylic acid (1-phenylethyl) amide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 1-phenylethylamine (56.1 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 100% ethyl acetate) afforded the desired product as a clear oil (78.7 mg, 99%).

compound #18 [1,6]naphthyridine-2-carboxylic acid (pyridine-2-ylmethyl) amide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 2-(aminomethyl)pyridine (45.3 μL, 0.431 mmol) and 1-(3-dimethylaminopropyl)-3ethylcarboiimide hydrochloride (61.8 mg, 0.316 mmol). The resulting mixture was allowed to stir at room temperature overnight and it was found to be clear. The solvent was removed under vacuum. Flash column chromatography of the residue (50% hexane/ethyl acetate to 5% methanol/ethyl acetate) afforded the desired product as a light brown solid (78.7 mg, 99%) m.p. 123–125° C.

compound #19 [1,6]naphthyridine-2-carboxylic acid cyclohexyl-methylamide

To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), cyclohexanemethylamine (57.2 μL, 0.431 mmol) and 1-(3-dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (100% ethyl acetate) afforded the desired product as a white solid (74.9 mg, 97%): m.p. 62–63° C.

compound #20 (3,4-dihydro-1h-isoquinolin-2-yl)-[1,6] naphthyridin-2-yl-methanone To a stirring mixture of 2-[1,6]naphthyridinecarboxylic acid (50 mg, 0.287 mmol) in anhydrous DMF (1.0 mL) at room temperature was added sequentially 1-hydroxybenzotriazole hydrate (42.7 mg, 0.316 mmol), 1,2,3,4-tetrahydroisoquinoline (55.6 μL, 0.431 mmol) and 1-(3dimethylaminopropyl)-3-ethylcarboiimide hydrochloride (61.8 mg, 0.316 mmol). The resulting mixture was allowed to stir at room temperature overnight and it was found to be clear. The solvent was removed under vacuum. Flash column chromatography of the residue (100% ethyl acetate) afforded the desired product as a white solid (79.1 mg, 95%): m.p. 98–100° C.

compound #21 N-(2-methylthiobenzyl)-2-[1,6] naphthyridine carboxamide

To a stirring mixture of 2-methylsulfanylbenzylamine hydrochloride (81.7 mg, 0.431) in anhydrous DMF (1.0 mL) was added triethylamine (60.0 μL, 0.431 mmol). After 5 minutes, 2-[1,6]naphthyridinecarboxylic acid (50 mg, 0.287 mmol), 1-hydroxybenzotriazole hydrate (42.7 mg, 0.316 mmol), and 1-(3-dimethylaminopropyl)-3-ethylcarboiimide hydrochloride (61.8 mg, 0.316 mmol) were added sequentially. The resulting mixture was allowed to stir at room temperature overnight. The solvent was removed under vacuum. Flash column chromatography of the residue (50% hexane/ethyl acetate to 100% ethyl acetate) afforded the desired product as a light brown solid (88.2 mg, 99%): m.p. 102–103° C.

compound #32 7,8-dihydroisoquinolin-6-carboxylic acid 2'-methoxybenzylamide step 1

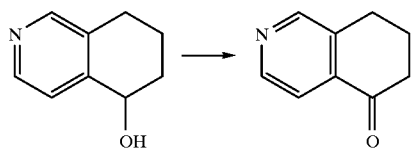

Chromium trioxide (15.50, 173.1o mmol) was added in one protion to a solution of pyridine (28 mL, 346.20 mmol) in dichloromethane (17% mL) at 0° C. The cooling bath removed and the mixture was allowed to stir for 30 min. To that solution was then added a solution of the alcohol (Cheng, C. Y.; Hsin, L. W.; Liou, J. P. *Tetrahedron*, 1996, 52, 10935). (3.851 g, 25.85 mmol) in dichloromethane (15 mL). The mixture was then stirred at room temperature for 2 h and the solution was decanted, the solvent was then removed and the residue was purified by chromatography eluting with 2% MeOH in CH$_2$Cl$_2$. The desired compound was obtained as a pale yellow solid (2.662 g, 70%)

$^1$H NMR (400 MHz,CDCl$_3$) δ: 8.69 (s, 1 H. H-1), 8.64 (d, 1 H. H-2, J=7.1 Hz), 7.78 (d, 1 H. H-4, J=7.L Hz), 2.99 (t, 2 H, H-6, J=6.2 Hz), 2.73 (t, 2 H. H-8, J=6.3 Hz), 2.21 (t, 2 H. H-7, J=6.2 Hz).

Step 2

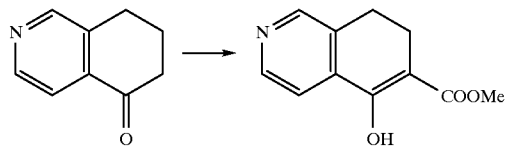

LiHMDS in THF (1M, 11.0 mL, 1 mmol) was added to a solution name (Lithrium 1,1,1,3,3,3-hexamethyldisilazane) of ketone (115 mg, 0.78 mmol) in THP (3 mL) at −78° C. After 15 min at this temperature methyl cyanoformate (0.3 mL, 3.9 mmol) was added and the mixture was allowed stir overnight. The reaction was then quenched with saturated ammonium chloride and extracted with ethyl acetate. After drying (Na$_2$SO$_4$). The residue was triturated with cold ethyl acetate yielding the desired compound. (75 mg, 47%) $^1$H NMR (400 MHz,CDCl$_3$) δ: 11.81 (s, 1 H, OH) 8.63 (d, 1 H, H-3, J=5.9 Hz), ), 8.58 (s, 1H. H-1), 8 (d, d H. H-4, J=5.9 Hz), 3.93 (s, 3 H, OCH$_3$), 3.05 (t, 2 H, H-8, J=7.8 Hz), 2.74 (t, 2 H, H-7, J=8.5 Hz)

Step 3

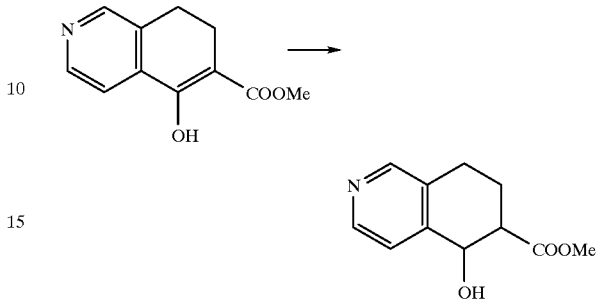

A solution of the enol from step 2 (350 mg, 1.71 mmol) in methanol (10 mL) was stirred in the presence of palladium on carbon (10%, 350 mg) under an atmosphere of hydrogen for 1 h. The catalyst was then removed by filtration through celite and the filtrate was concentrated to dryness to give the desired compound as a white solid. (350 mg, 100%)

$^1$H NMR (400 MHz,DMSO) δ: 8.72 (s, 1 H, H-1), 8.67 (d, 1 H, H-3, J=5.8 Hz), ), 7.90 (d, 1 H. H-4, J=5.8 Hz), 6.6 (br, 1 H, OH), 5.02 (d, 1 H, H-5, J=4.3 Hz), 3.63 (s, 3 H, OCH$_3$), 3.0 (m, 2 H), 2.8 (m, 1 H), 2.0 (m, 1 H), 1.9 (m, 1 H).

Step 4

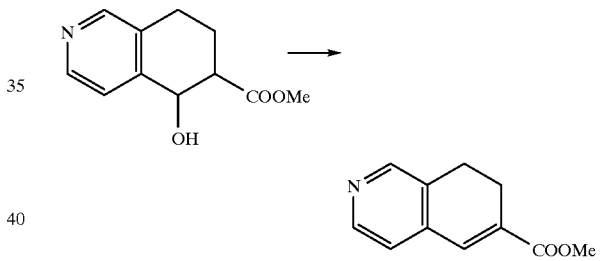

Methanesulfonyl chloride (0.18 ML, 2.37 mmol) was added to a solution of alcohol from step 3 (350 mg, 1.69 mmol) and triethylamine (0.35 mL, 2.54 mmol) in dichloromethane (10 mL) at 0° C. The mixture was then stirred at room temperature for 2 h and the solution was then washed with water, NaHCO$_3$ and dried using Na$_2$SO$_4$. The solvent was then removed and the residue was taken into dichloroethane (5 mL) and treated with DBU (1,8-diazabicyclo [5.4.0]undec-7-ene) (0.5 mL). The solution was stirred for 2 h at room temperature and the solvent was removed under vacuo and the residue was purified by chromatography (1% MeOH in CH$_2$Cl$_2$) to give the desired compound (159 mg, 50% from alcohol)

$^1$H NMR (300 MHZ,CDCl$_3$) δ: 8.46 (d, 1 H, H-3, J=4.4 Hz), 8.44 (s, 1 H, H-1), 7.44(s, 1 H, H-5), 7.06 (d, 1 H, H-4, J=4.4 Hz), 3.83 (s, 3 H, OCH$_3$), 2.87 (t, 2 H, H-8, J=8.0 Hz), 2.69 (t, 2 H, H-7, J=8.0 Hz).

Step 5

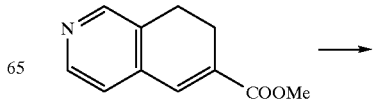

21
-continued

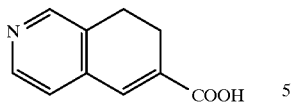

NaOH (1N, 1.3 mL, 1.3 mmol) was added to a solution of ester from step 4 (159 mg, 0.84 mmol) in dioxane (3 mL) at rt. After 3 h, the mixture was concentrated to about 1 mL and HCl (6N) was carefully added to the ice cold solution until pH5 was reached. The resulting precipitate was collected, washed with water and dried under vacuo (92 mg, 62%)

$^1$H NMR (400 MHz,DMSO) δ: 8.42 (m, 2 H, H-1 and H-3), 7.45 (s, 1 H, H-5), 7.31 (d, 1 H, H-4, J=4.9 Hz), 2.82 (t, 2 H, H-8, J=8.2 Hz), 2.53 (t, 2 H, H-7, J=7.5 Hz).

Step 6

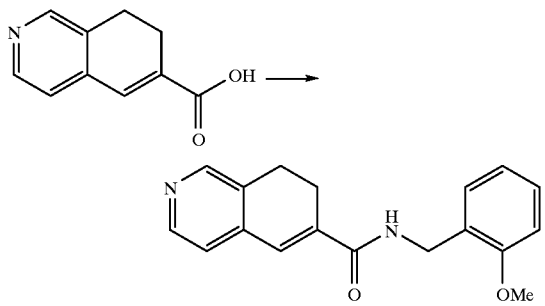

A solution of the acid from step 5 (60 mg, 0.34 mmol), 1-(3-dimethylaminopropyl)-3-ethylcarbodiimide hydrochloride (79 mg, 0.41 mmol), and HOBT (1-hydroxybenzotriazole hydrate) (55 mg, 0.41 mmol) 2-methoxybenzylamine (54 μL, 0.41 mmol) in DMF (1 mL) was stirred at room temperature for 24 h. The solvent was then removed under vacuo and the residue was purified by chromatography eluting with 50–100 EtAC in Hexanes. The desired compound was obtained as a white solid. (80 mg, 79%)

$^1$H NMR (300 MHz, CDCl$_3$) δ: 8.45 (d, 1 H, J=4.8 Hz), 8.41 (s, 1 H, H-1), 7.31 (m, 2 H), 7.10 (s, 1 H, H-5), 7.03 (d, 1 H, H-4, J=4.8 Hz)6.94 (br, 1 H, NH), 4.59 (d, 2 H, CH$_2$, J=5.8 Hz), 3.91 (s, 3 H, OCH$_3$), 2.88 (t, 2 H, H-8, J=8.0 Hz), 2. 64 (t, 2 H, H-7, J=8.3 Hz).

compound #33 8-bromo-[1,6]Naphthyridine-2-carboxylic acid 2-N-ethylaminobenzylamide
step 1
N-ethyl-2-aminobenzonitrile

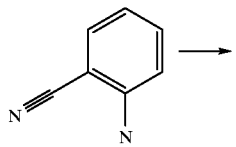

22
-continued

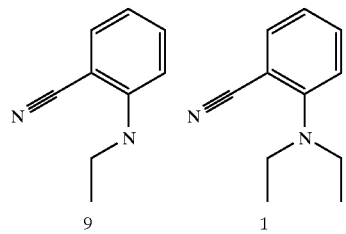

A solution of lithium bis(trimethylsylil)amide (7.6 mL, 1M in tetrahydrofurane) is added to a cold (0° C.) solution of 2-aminobenzonitrile (1 g, 8.5 mmol) in tetrahydrofuran (10 mL) and DMF (2 mL). The resulting solution is stirred for 30 minutes, iodoethane (0.68 mL, 8.5 mmol) was then added dropwise. The solution is allowed to reach room temperature and stirred over night. The reaction mixture was then quenched with saturated NH$_4$Cl evaporated, diluted with CH$_2$Cl$_2$, washed with water, brine and t-he combined organic extracts were dried with Na$_2$SO$_4$ and concentrated. The resulting liquide was chromatographed onto silica gel (30% EtOAc-Hex), giving the title compound in a 9 to 1 ratio of mono and bis alkylated compounds non separable.

N-ethyl-2-aminobenzonitrile
$^1$H NMR (400MHz) (CDCl$_3$) δ: 7.41–7.33 (m, 2H, Ph), 6.68–6.65 (m, 2H, Ph), 4.5 (s, 1H, NH), 3.29–3.22 (m, 2H, CH$_2$N), 1.32(t, J=7 Hz, 3H, CH$_3$CH$_2$)

N-diethyl-2-aminobenzonitrile
$^1$H NMR (400 MHz) ( CDCl$_3$) δ: 7.41–7.33 (m, 2H, Ph), 6.68–6.65 (m, 2H, Ph), 4.5 (s, 1H, NH), 3.41 (q, 4H, CH$_2$N) 1.20(t, J=7 Hz, 6H, CH$_3$CH$_2$)

step 2
N-ethyl-2-aminobenzylamine dihydrochloride and N-diethyl-2-aminobenzamine dihydrochloride

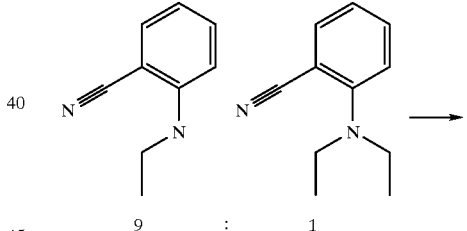

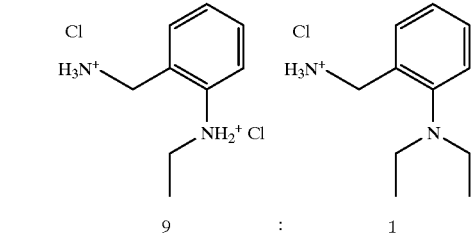

N-ethyl-2-aminobenzonitrile (0.4 g, 2.7 mmol), 10% Pd/C (100 mg) is added in a dry flask followed by ethanol (15 mL). To this solution HCl was added (2.7 mL, 4M in dioxane) . The resulting reaction was placed under an H$_2$(g) atmosphere. The resulting solution was filtered over celite, was evaporated, triturated with ether, and the solvent was evaporated to yield the above intermediate.

N-ethyl-2-aminobenzylamine dihydrochloride
$^1$H NMR (400MHz)(DMSO) δ: 8.5–8.2 (m, 3H, NH$_3$), 7.35–7.25 (1, 2H, Ph), 7.34(t, J=7.5 Hz, 1H, Ph) 7.1–6.9 (m, 2H, Ph), 4.07 (s, 2H, CH$_2$N), 3.19 (q, 2H, J=7 Hz, CH$_3$CH$_2$), 1.27(t, J=7 Hz, 3H, CH$_3$CH$_2$)

N-diethyl-2-aminobenzamine dihydrochloride

1H NMR (400MHz)(DMSO) δ: 8.5–8.2 (m, 3H, NH,) 7.35–7.25 (1, 2H, Ph), 7.34(t, J=7.5 Hz, 1H, Ph) 7.1–6.9 (m, 2H, Ph) 4.07 (s, 2H, CH₂N), 3.33 (q, 2H, J=7 Hz, CH₃CH₂), 1.07(t, J=7 Hz, 3H, CH₃CH₃)

step 3

8-bromo-[1,6]Naphthyridine-2-carboxylic acid

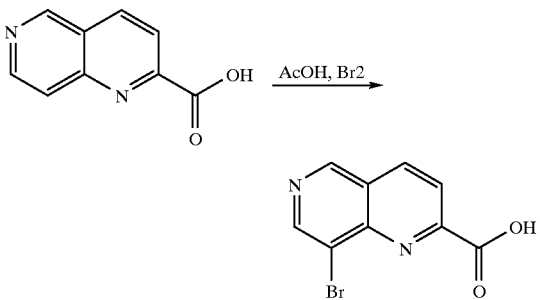

is added Br₂ over 40 minutes to a suspension of the [1,6]Naphthyridine-2-carboxylic acid (3 g,17.25 mmol) in acetic acid (150 mL) at room temperature (18.96 mmol). The solution was stirred over night at room temperature then the mixture was quenched with ice and stirred for 1 hour. The suspension was evaporated to dryness then triturated, filtrated and washed with a minimum of cold water. The resulting composition was dried under vacuum over night to yield the title compound in a 59% yield ¹H NMR (400MHz)(DMSO) δ: 14.1–13.8 (M, 1H, COOH), 9.49 (s, 1H, H5), 9.10 (s, 1H, H7), 8.83 (d, 1H, J=8.5 Hz, H4), 8.31 (d, 1H, J=8.5 Hz, H3)

step 4

8-bromo-[I,6]Naphthyridine-2-carboxylic acid 2-N-ethylamino-benzylamide

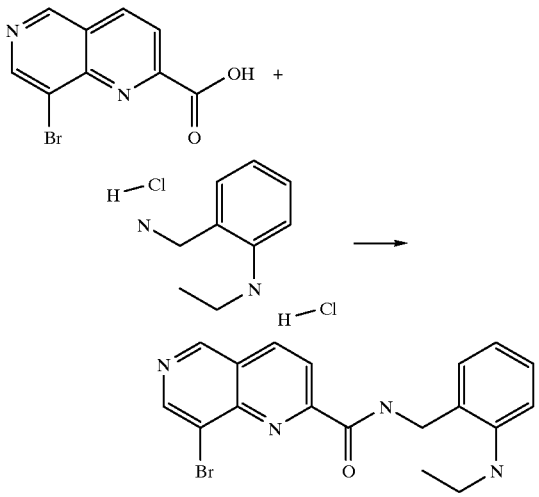

Triethylamine (0.095 mL, 0.68 mmol) was added to a solution of the salt (57 mg, 0.255 mmol) in DMF (1.5 mL) at room temperature. The solution was stirred for five minutes. Simultaneously, the acid (30 mg, 0.12 mmol), HOBT (25 mg, 0.19 mmol) and EDCI were added (36 mg, 0.19 mmol) The reaction was left to stir over night at room temperature. The solution was evaporated to dryness and the residue was dissolved in a minimum of CH₂Cl₂ and purified using flash chromatography (50% AcOEt/Hexane to 100% AcOEt) to yield the title compound in a 61% yield.

¹H NMR (400MHz) (CDCl₃) δ: 9.27 (s, 1H, H5), 9.05 (s, 1H, H7), 8.65–8.55 (s, 1H, NH), 8.55–8.45 (m, 2H, H4 and H3), 7.3–7.2 (m, 2H, Ph), 7.85–7.65 (m, 2H, Ph), 4.67 (d, 2H, J=6.5 Hz, CH₂), 3.25–3.15 (m, 2H, CH₂CH₃), 1.4–1.3 (m, 3H, CH₃CH₂)

step 5

8-bromo-[1,6]Naphthyridine-2-carboxylic acid 2-N-ethylaminobenzylamide hydrochloride salt

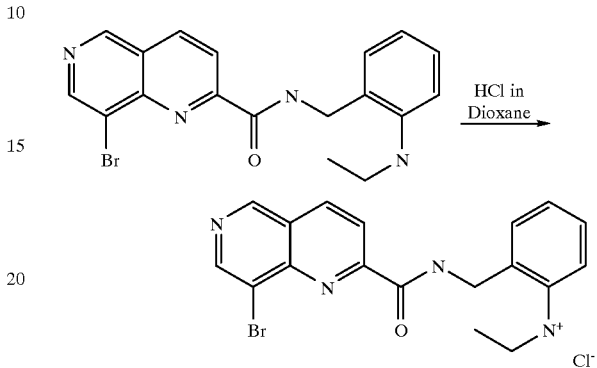

HCl was added Lo a solution of the amide (23.4 mg, 0.06 mmol) in CH₂Cl₂ (0.5 mL) at room temperature (1 mL, 4M in dioxane) The solution was stirred for 20 minutes at room temperature. The suspension was evaporated to dryness then triturated in ether to yield the title compound in a quantitative yield.

1H NMR (400MHz) (CDCl₃) δ: 9.27 (s, 1H, H5) 9.05 (s, 1H, H7), 8.65–8.55 (s, 1H, NH), 8.55–8.45 (m, 2H, H4 and H3), 7.3–7.2 (m, 2H, Ph), 7.85–7.65 (m, 2H, Ph), 4.67 (d, 2H, J=6.5 Hz, CH₂), 3.25–3.15 (m, 2H, CH₂CH₃), 1.4–1.3 (m, 3H, CH₃CH₂)

compound #39 [1,6]Naphthyridine-2-thiocarboxylic acid-2-trifluoromethylbenzylamide;

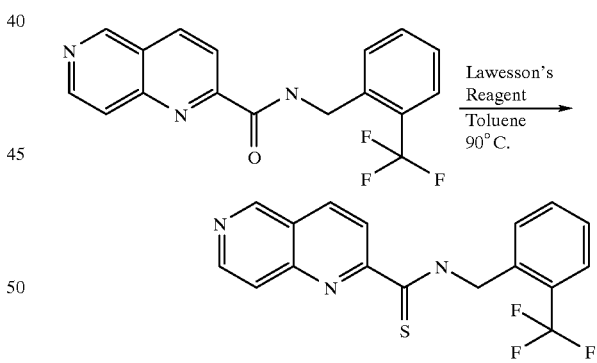

Lawesson's reagent was added to a stirring solution of BCH-5024 (30mg, 0.09 mmol) in toluene(1.5 mL) (38 mg, 0.09 mmol). The solution was then heated to 90° C. for 1 h. The solvent was evaporated and the product was purified by flash chromatography (50% AcOEt/He to 100% AcOEt) to yield 25.8 mg of the thioamide derivative.

¹H NMR (400MHz, CDCl₃): 10.55 (bs, 1H), 9.3 (s, 1H), 9.0 (d, J=8.5 Hz, 1H), 8.81 (d, J=6Hz, 1H), 8.44(d, J-8.5 Hz, 1H), 7.90 (d, J=6.0 Hz, 1H) 7.75 (d, J=7.5 Hz, 1H), 7.68 (d, J 7.5 Hz, 1H), 7.56 (t, J=7.5Hz, 1H), 7.46 (t, J=7.5Hz, 1H), 5.37 (d, J=6 Hz, 2H).

compound #46 1-(2-iso-propoxy phenyl)-3-[1,6] naphthyridin-2 yl-urea;

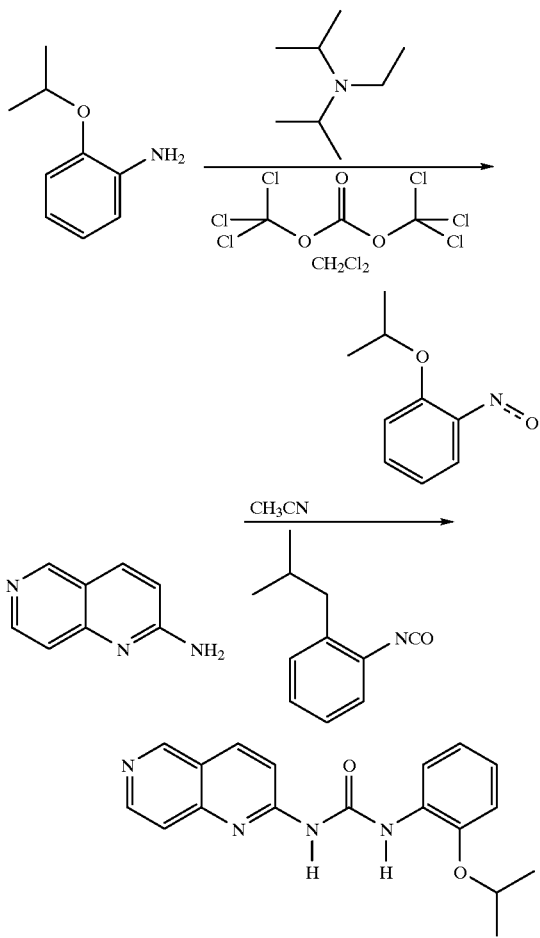

A solution of 2-isopropoxyphenylamine (400 mg, 2.64 mmol) and N,N-diisopropylethylamine (1.02 ml, 5.82 mmol) in dichloromethane (10.0 mL) was added dropwise via cannula to a solution of triphosgene (274.7 mg, 0.93 mmol) in dichloromethane (6.0 mL) at −78° C. The solution was stirred at −78° C. for 1 hour, then at 0° C. for 1 hour, and then at room temperature for 1 hour. The mixture was concentrated, triturated with pentane, and then filtered. The desired isocyanate was Isolated as a (brown oil (449.7 mg, 96%): $^1$H NMR (400 MHz, CDCl$_3$) δ7.12 (1H, Ph), 6.99 (1H, Ph), 6.90 (1H, Ph), 6.86 (1H, Ph), 4.65 (septet, 1H, CH, J 6.5 Hz), 1.42 (d, 6H, CH$_3$, J 6.5 Hz) ppm.

A mixture of the isocyanate (45.8 mg, 0.253) and the amine (25 mg, 0.172) in acetonitrile (1 mL) was heated at reflux for 3 hours. The solvent was removed using a rotoevaporator. The residue was then triturated with diethyl ether, filtered, and washed with diethyl ether. The solid was washed again with ethanol and then diethyl ether repeatedly. The desired product was isolated as a light brown solid (34.4 mg, 62%): m.p. >200° C.; $^1$H NMR (400 MHz, DMSO) δ11.33 (bs, 1H, NH), 10.56 (bs, 1H, NH), 9.17 (s, 1H, H-5), 8.68 (d, 1H, H-7, J 5.8 Hz), 8.43 (d, 1H, H-4, J 8.9 Hz), 8.16 (1H, Ph), 7.68 (d, 1H, H-8, J 5.8 Hz), 7.50 (d, 1H, H-3, J 8.9 Hz), 7.12 (1H, Ph), 7.03 (1H, Ph), 6.93 (1H, Ph), 4.70 (septet, 1H, CH, J 6.0 Hz), 1.34 (d, 6H, CH$_3$, J 6.0 Hz) ppm.

In a like manner, the following compounds were prepared:

Compound #22 N-(2-hydroxybenzyl)-2-(1,6) naphthyridinecarboxamide;

compound #23 N-(2-methoxycarbonylbenzyl)-2-(1,6) naphthyridinecarboxamide;

compound #26 N-(2propoxybenzyl)-2-[1,6]naphthyridine-2-carboxamide;

compound #27 (2{[([1,6]naphthyridine-2-carbonyl)-amino]-methyl}-phenyl)-carbonic acid tert-butyl ester;

compound #28 [1,6]Naphthyridine-2-carboxylic acid (2,3,4,5-tetrahydrobenzo[B]oxepin-5-yl)-amide;

compound #29 [1,6]Naphthyridine-2-carboxylic acid (chroman-4-yl)-amide;

compound #30 N-(2'-methoxybenzyl)-5-amino-2-[1,6] naphthyridinecarboxamide;

compound #31 [1,6]Naphthyridine-2-carboxylic acid 2,3-(methylenedioxy)-benzylamide;

compound #33 8-bromo-[1,6]naphthyridine-2-carboxylic acid (2-N-ethylaminobenzylamide);

compound #34 8-bromo-[1,6]naphthyridine-2-carboxylic acid (2-isopropoxybenzylamide);

compound #35 8-bromo-[1,6]naphthyridine-2-carboxylic acid (2-methoxybenzylamide);

compound #36 8-chloro-[1,6]naphthyridine-2-carboxylic acid (2-isopropoxybenzylamide);

compound #37 8-chloro-[1,6]naphthyridine-2-carboxylic acid (2-N-ethylaminobenzylamide);

compound #38 8-(2pyridyl)-[1,6]naphthyridine-2-carboxylic acid (2--isopropoxybenzylamide);

compound #40 [1,6]Naphthyridine-2-thiocarboxylic acid-2-isopropoxybenzylamide;

compound #41 [1,6]Naphthyridine-2-thiocarboxylic acid-3-methoxybenzylamide;

compound #42 8-bromo-[1,6]Naphthyridine-2-thiocarboxylic acid-2-isopropoxybenzylamide;

compound #43 [1,6]Naphthyridine-2-thiocarboxylic acid 2-methoxy-benzylamide;

compound #44 [1,6]Naphthyridine-2-thiocarboxylic acid 2-ethoxy-benzylamide;

compound #45 [1,6]Naphthyridine-2-thiocarboxylic acid-2methoxy-cyclohexylmethyl-amide, compound #47 1-(2-iso-propoxybenzyl)-3-[1,6] naphthyridin-2-yl-urea;

compound #48 1-(N-boc-4-aminobutyl)-3-[1,6]-naphthyridin-2-yl-urea;

compound #49 1-(4-aminobutyl)-3-[1,6]naphthyridin-2-yl-urea hydrochloride;

compound #50 1-[(S)-α-methylbenzyl]-3-[1,6] naphthyridin-2-yl-urea;

compound #51 1-[(R)-α-methylbenzyl]-3-[1,6] naphthyridin-2-yl-urea;

compound #52 1-(2-methoxy-phenyl)-3-[1,6]naphthyridin-2-yl-urea;

compound #53 1-butyl-3-[1,6]naphthyridin-2-yl-urea;

compound #54 1-(2-methoxybenzyl)-3-[1,6]naphthyridin-2-yl-urea;

compound #55 1-(2-ethoxy-phenyl)-3-[1,6]naphthyridin-2-yl-urea;

Compound #56 1-(2-methyl-phenyl)-3-[1,6]naphthyridin-2-yl-urea; and

Compound #57 8-(2-pyridyl)-[1,6]naphthyridine-2-carboxylic acid (2-isopropoxybenzylamide).

The following compounds were obtained commercially (Peakdale Fine Chemicals Limited, Glossop Derbyshire, UK):

compound #24 (1,6)naphthyridine-2-carboxylic acid allylamide (PFC-029);

compound #25 N-(2-methoxybenzyl)-2-(1,6) naphthyridinecarboxamide (PFC-032).

EXAMPLE 2

CMV Plaque Reduction Assay

The anti-CMV activity of test compounds was evaluated in a plaque reduction assay as follows:

In 12-well tissue culture dishes, 1.5X10E5 or Hs68 cells (human lung fibroblast cell line) were plated per well with 2 ml of DMEM 10% fetal bovine serum and incubated in 5% $CO_2$/air at 37° C. overnight or until cells were ready.

The medium was then removed and the cells inoculated with 0.5 ml (containing 200 pfu/ml diluted in DMEM 2% FBS) of HCMV virus in each well.

After adsorption at 37° C. for 2 hours, the virus was removed and cell monolayers were overlaid (1 ml) with DMEM 2% FBS containing test compounds at various concentrations. The cells were then incubated at 37° C. for 8 days, and then fixed with one volume (1 ml) of formaldehyde 8%/water or PBS 1X for 30 minutes.

The formaldehyde solution was removed and the cell monolayers were stained with crystal violet 2%/EtOH 20% for a few seconds and then rinsed with water.

Monolayers were examined for the presence of plaques under a microscope, the percentage of plaque reduction determined for each compound by comparison with the untreated cells (no test compound) and the 50% inhibitory concentration ($IC_{50}$) established. Ganciclovir was used as a positive control.

Note: DMEM medium contained 1% glutamine and 1% pen/strep

EXAMPLE 3

Cytotoxicity Assay

The cytotoxicity of test compounds was evaluated according to the following procedure:

Flat bottom 96 well plates were plated with 5X10E3 Vero-34 cells/well and 1X10E4 Hs-68 or Wi-38 cells/well respectively and incubated overnight at 37° C. and 5% $CO_2$/air. After incubation, the supernatant medium was removed and replaced with test compound dilutions in 2% DMEM (150 ul). The cells were then incubated 48 hours in a 5% $CO_2$ incubator at 37° C.

50 µl/well of 10 uCi/ml solution of [3H]-methyl thymidine (specific activity of approx. 2Ci/mmol) was added to the culture medium and incubated overnight (18 hours) in a 5% $CO_2$ incubator at 37° C.

Cells were then collected onto a fiberglass filter (Printed Filtermat A 1450-421 Wallac) with a Tomtec cell harvester. Suspended cells were collected directly onto filter while for adherent cells, the medium was first removed, then the cells washed with PBS and trypsinized for 2–3 minutes (50 µl trypsin/well) before collecting.

Filters were dried for 1 hour at 37–40° C. and then placed into bags (1450-microbeta 4 1450-432 Wallac) with 4.5ml of Betascint and counts obtained with Microbeta 1450 Wallac (protocol 1).

The percent of cell proliferation was determined by comparison to the control (not test compound) and thereby establishing 50% inhibitory concentration is established.

Compounds according to the invention where found to inhibit CMV according to the plaque reduction assay and compared favorably to ganciclovir. Results are summarized in table 1. The compounds were tested in tandem with ganciclovir which consistently showed an $IC_{50}$ of >0.1<0.5 µg/ml and a $CC_{50}$ which varied from −10 to 200 µg/ml.

TABLE 1

|   |   |   | $IC_{50}$ (ug/ml) | $CC_{50}$ (ug/ml) |
|---|---|---|---|---|
| #1 | 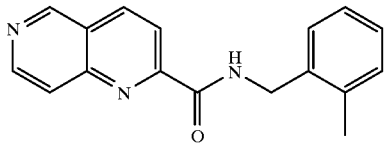 | N-(2-methylbenzyl)-2-(1,6)-naphthyridinecarboxamide | ~1 | >50 <75 |
| #2 | 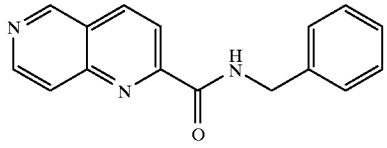 | N-benzyl-2-(1,6)naphthyridine-carboxamide | ~1 | ~50 |
| #3 | 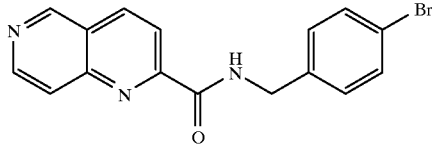 | N-(4-bromobenzyl)-2-(1,6)-naphthyridinecarboxamide | >10 <50 | >10 <50 |

TABLE 1-continued

| | | | IC$_{50}$ (ug/ml) | CC$_{50}$ (ug/ml) |
|---|---|---|---|---|
| #4 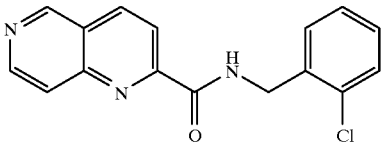 # | | N-(2-chlorobenzyl)-2-(1,6)-naphthyridinecarboxamide | >0.5 <1 | ~100 |
| #5 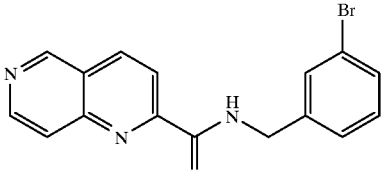 # | | N-(2-bromobenzyl)-2-(1,6)-naphthyridinecarboxamide | >0.5 <1 | >100 |
| #6 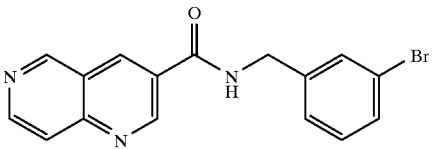 # | | N-(3-bromobenzyl)-2-(1,6)-naphthyridinecarboxamide | >1 <5 | ~50 |
| #7 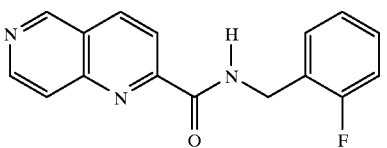 # | | N-(2-fluorobenzyl)-2-(1,6)-naphthyridinecarboxamide | <5 | ~100 |
| #8 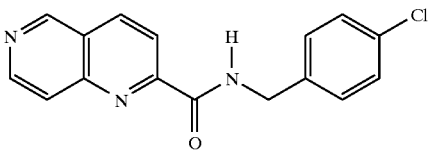 # | | N-(4-chlorobenzyl)-2-(1,6)-naphthyridinecarboxamide | >1 <10 | >6.25 <10 |
| #9 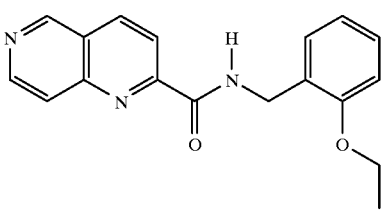 # | | N-(2-ethyloxybenzyl)-2-(1,6)-naphthyridinecarboxamide | ~0.1 | ~6.25 |
| #12 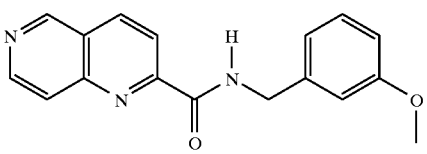 # | | N-(3-methoxybenzyl)-2-(1,6)-naphthyridinecarboxamide | <5 | >100 |

TABLE 1-continued

| | | | IC$_{50}$ (ug/ml) | CC$_{50}$ (ug/ml) |
|---|---|---|---|---|
| #13 | 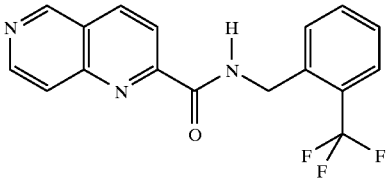 | N-(2-trifluoromethylbenzyl)-2-(1,6)naphthyridinecarboxamide | <5 | >100 |
| #14 | 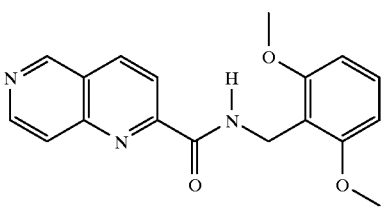 | N-(2,6-dimethoxybenzyl)-2-(1,6)naphthyridinecarboxamide | <5 | >100 |
| #15 | 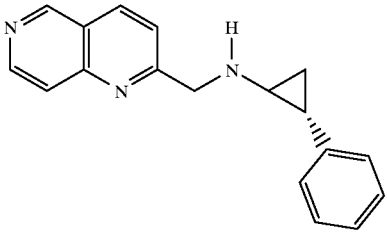 | [1,6]naphthyridine-2-carboxylic acid (trans-2-phenyl-cyclopropyl)amide | >1 <10 | ~25 |
| #16 | 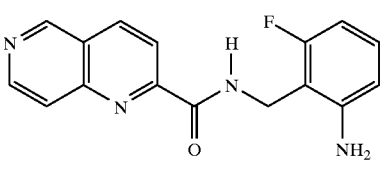 | N-(2-fluoro-5-aminobenzyl)-2-(1,6)naphthyridinecarboxamide | >1 <10 | ~25 |
| #17 | 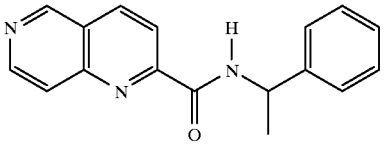 | [1,6]naphthyridine-2-carboxylic acid (1-phenylethyl) amide | >0.1 <1 | >25 <50 |
| #18 | 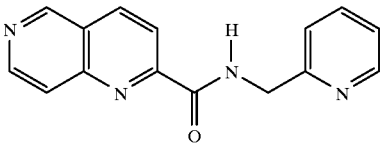 | [1,6]naphthyridine-2-carboxylic acid (pyridine-2-ylmethyl) amide | >5 <25 | >100 |
| #19 | 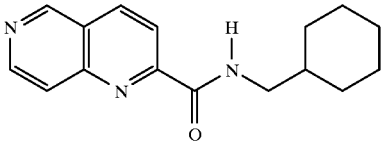 | [1,6]naphthyridine-2-carboxylic acid cyclohexylmethylamide | >1 <10 | >25 <50 |

TABLE 1-continued

| | | | IC$_{50}$ (ug/ml) | CC$_{50}$ (ug/ml) |
|---|---|---|---|---|
| #20 | | (3,4-dihydro-1H-isoquinolin-2-yl)-[1,6]naphthyridin-2-yl-methanone | >5 <25 | >100 |
| #21 | | N-(2-methylthiobenzyl)-2-(1,6)-naphthyridinecarboxamide | >1 <10 | ~50 |
| #22 | | N-(2-hydroxybenzyl)-2-(1,6)-naphthyridinecarboxamide | <5 | >25 <100 |
| #23 | | N-(2-methoxycarbonylbenzyl)-2-(1,6)naphthyridinecarboxamide | <5 | >100 |
| #24 | | (1,6)naphthyridine-2-carboxylic acid allylamide | >5 <10 | >10 <100 |
| #25 | | N-(2-methoxybenzyl)-2-(1,6)-naphthyridinecarboxamide | >0.3 <1.5 | >120 <150 |
| #26 | | N-(-2-propoxybenzyl)-2-[1,6]-naphthyridine-2-carboxamide | >0.005 <0.01 | ~1.5 |

TABLE 1-continued

| | | | IC$_{50}$ (ug/ml) | CC$_{50}$ (ug/ml) |
|---|---|---|---|---|
| #32 | (structure) # | 7,8-dihydroisoquinolin-6-carboxylic acid 2-methoxybenzylamide | >0.1 <1 | >50 <100 |
| #33 | (structure) # | 8-bromo-[1,6]naphthyridine-2-carboxylic acid (2-N-ethyl-aminobenzylamide) | <0.01 | >6.25 <12.5 |
| #34 | (structure) # | 8-bromo-[1,6]naphthyridine-2-carboxylic acid (2-isopropoxy-benzylamide) | >0.1 <1 | ~12.5 |
| #35 | (structure) # | 8-bromo-[1,6]naphthyridine-2-carboxylic acid (2-methoxy-benzylamide) | ~0.01 | ~12.5 |
| #40 | (structure) # | [1,6]Naphthyridine-2-thio-carboxylic acid-2-isopropoxy-benzylamide; | >0.1 <1 | >12.5 <25 |
| #41 | (structure) # | [1,6]Naphthyridine-2-thio-carboxylic acid-3-methoxy-benzylamide; | >1 <10 | >25 <50 |

TABLE 1-continued
| | | | IC$_{50}$ (ug/ml) | CC$_{50}$ (ug/ml) |
|---|---|---|---|---|
| #46 | 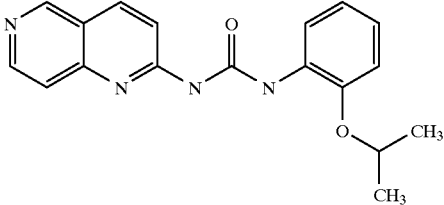 | 1-(2-iso-propoxyphenyl)-3-[1,6]-naphthyridin-2-yl-urea; | ~0.01 | ~25 |
| #47 | 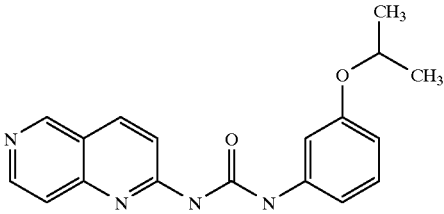 | 1-(2-iso-propoxybenzyl)-3-[1,6]-naphthyridin-2-yl-urea; | >0.01 <0.1 | >25 <50 |
| #48 | 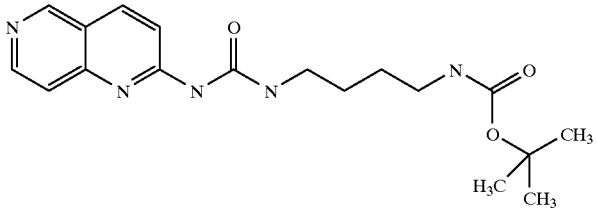 | 1-(N-boc-4-aminobutyl)-3-[1,6]-naphthyridin-2-yl-urea; | >0.1 <1 | >3.15 <6.25 |
| #49 | 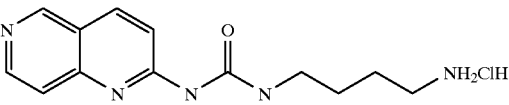 | 1-(4-aminobutyl)-3-[1,6]-naphthyridin-2-yl-urea hydrochloride; | >1 <5 | >6.25 <12.5 |
| #50 | 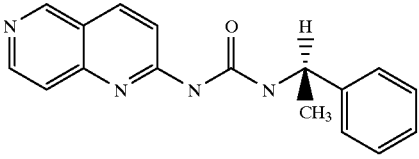 | 1-[(S)-α-methylbenzyl]-3-[1,6]-naphthyridin-2-yl-urea; | >1 <10 | >12.5 <25 |
| #51 | 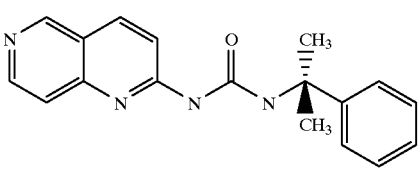 | 1-[(R)-α-methylbenzyl]-3-[1,6]-naphthyridin-2-yl-urea; | >0.01 <0.1 | <3.15 |
| #53 | 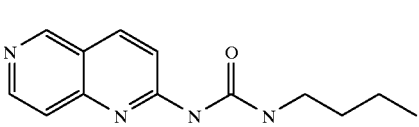 | 1-butyl-3-[1,6]naphthyridin-2-yl-urea; | >0.1 <1 | >2.5 <5 |

TABLE 1-continued

| | | IC$_{50}$ (ug/ml) | CC$_{50}$ (ug/ml) |
|---|---|---|---|
| #56 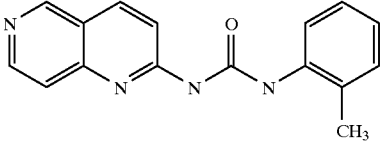 | 1-(2-methylphenyl)-3-[1,6]-naphthyridin-2-yl-urea | ~1 | >100 |
| #57 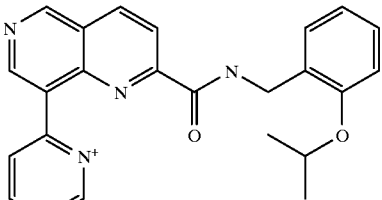 | 8-(2-pyridyl)-[1,6]-naphthyridine-2-carboxylic acid (2-isopropoxybenzylamide); | >0.1 <1 | >6 <12.5 |

We claim:

1. A method of inhibiting cytomegalovirus replication in a mammal comprising administering to said mammal an anti-cytomegaloviral amount of a compound of formula (I):

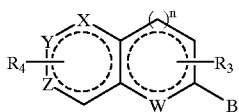

(I)

wherein
W is selected from, N and NR$_5$;
one of X, Y, and Z is N or NR$_5$ while the other two are independently selected from CH, CR$_4$, CH$_2$, C=O and CHR$_4$;
B is selected from the group consisting of;

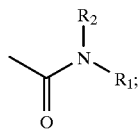

(II)

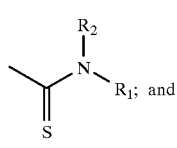

(III)

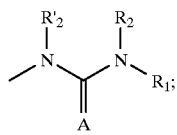

(IV)

wherein;
A is O or S;
R$_1$ is selected from:

C$_{1-6}$ alkyl, C$_{2-6}$ alkenyl or C$_{3-7}$ cycloalkyl optionally substituted with OH, halogen, amino, carboxyl or saturated or unsaturated C$_{3-10}$ (carbocycle or heterocycle) optionally substituted with OH, halogen, amino, mercapto, carboxy, C$_{14}$ (alkyl, alkoxy, alkylthio, acyl, acyloxy or alkoxycarbonyl) optionally substituted with OH, halogen, amino or C$_{1-4}$ alkoxy,; and C$_{3-7}$ cycloalkyl fused to C$_{6-10}$ aryl optionally substituted with OH, halogen, amino, mercapto, carboxy, C$_{1-4}$ (alkyl, alkoxy, alkylthio, acyl, acyloxy or alkoxycarbonyl) optionally substituted with OH, halogen, amino or C$_{1-4}$ alkoxy;

R$_2$ and R'$_2$ are independently selected from H, or C$_{1-4}$ alkyl or R$_1$ and R$_2$ together form a saturated or unsaturated 5 or 6 member heterocycle optionally fused to C$_{6-10}$ aryl or heteroaryl;

R$_3$ and R$_4$ are independently selected from H, OH, halogen, amino, cyano, C$_{1-6}$ (alkyl, alkoxy, acyl, acyloxy or alkoxycarbonyl) optionally substituted with OH, halogen, amino or C$_{1-4}$ alkoxy, and saturated or unsaturated C$_{3-10}$ (carbocycle or heterocycle) optionally substituted with OH, halogen, amino, mercapto, C$_{1-6}$ alkylthio, C$_{1-4}$ alkoxycarbonyl, halo-substituted C$_{1-4}$ alkyl or halo-substituted C$_{1-4}$ alkoxy, C$_{1-4}$ alkyl, C$_{1-4}$ alkoxy or carboxy;

R$_5$ is H, C$_{1-6}$ alkyl or C$_{1-6}$ acyl optionally substituted with OH, halogen, amino or C$_{1-4}$ alkoxy; and n is 0, 1 or 2.

2. A method according to claim 1, wherein Y is N or NR$_5$ and X and Z are independently selected from CH, CR$_4$, CH$_2$, C=O and CHR$_4$.

3. A method according to claim 1, wherein R is benzyl optionally substituted with one or two substituents selected from hydroxy, amino, halogen, C$_{1-4}$ alkyl, C$_{1-4}$ alkoxy, C$_{1-4}$ alkoxycarbonyl, C$_{1-4}$ alkylthio, C$_{1-4}$ halo-substituted alkyl.

4. A method according to claim 1, wherein R$_2$ and R'$_2$ is H.

5. A method according to claim 1 wherein R$_3$ is H.

6. A method according to claim 1, wherein R$_4$ is H.

7. An anti-cytomegalovirus composition comprising a pharmaceutically acceptable carrier, diluent or adjunct and a compound of formula (I) or a pharmaceutically acceptable salt thereof:

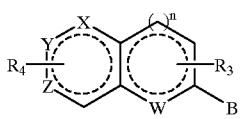
(I)

wherein
W is selected from N and $NR_5$;
one of X, Y, and Z is N or $NR_5$ while the other two are independently selected from CH, $CR_4$, $CH_2$, C=O and $CHR_4$;
B is selected from the group consisting of;

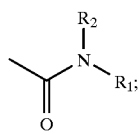
(II)

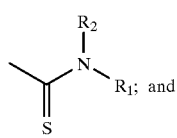
(III)

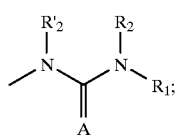
(IV)

wherein;
A is O or S;
$R_1$ is selected from:
  $C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$, alkoxy,; and
  $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_2$ and $R'_2$ are idependently selected from H, or $C_{1-4}$ alkyl or $R_1$ and $R_2$ together form a saturated or unsaturated 5 or 6 member heterocycle optionally fused to $C_{6-10}$ aryl or heteroaryl;
$R_3$ and $R_4$ are independently selected from H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{3-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;
$R_5$ is H, $C_{1-6}$ alkyl or $C_{1-6}$ acyl optionally substituted with OH, halogen, amino or $C_{1-4}$ alkoxy; and n is 0, 1 or 2.

8. A composition according to claim 7, wherein Y is N or $NR_5$ and X and Z are independently selected from CH, $CR_4$, $CH_2$, C=O and $CHR_4$.

9. A composition according to claim 7, wherein $R_1$ is benzyl optionally substituted with one or two substituents selected from hydroxy, amino, halogen, $C_{1-4}$ alkyl, $C_{1-4}$ alkoxy, $C_{1-4}$ alkoxycarbonyl, $C_{1-4}$alkylthio, $C_{1-4}$ halo-substituted alkyl.

10. A composition according to claim 7, wherein $R_2$ and $R'_2$ are H.

11. A composition according to claim 7, wherein $R_3$ is H.

12. A composition according to claim 7, wherein $R_4$ is H.

13. A compound of formula (I) and pharmaceutical acceptable salts thereof:

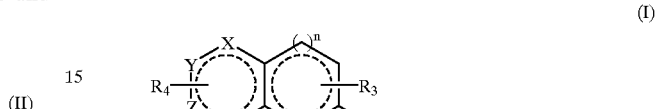
(I)

wherein
W is selected from N and $NR_5$;
one of X, Y, and Z is N or $NR_5$ while the other two are independently selected from CH, $CR_4$, $CH_2$, C=O and $CHR_4$;
B is selected from the group consisting of;

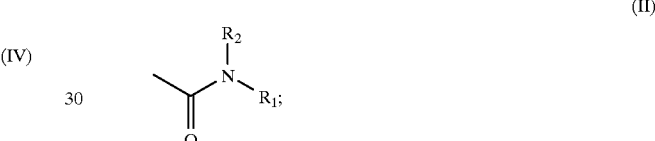
(II)

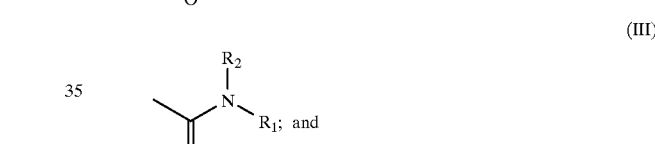
(III)

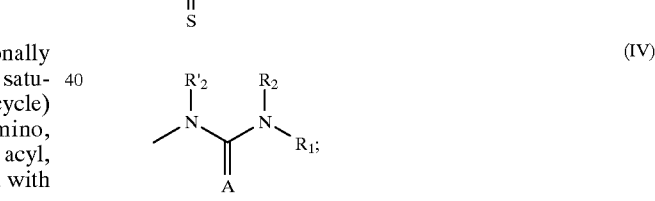
(IV)

wherein
A is O or S;
$R_1$ is selected from:
  $C_{1-6}$ alkyl, $C_{2-6}$ alkenyl or $C_{3-7}$ cycloalkyl optionally substituted with OH, halogen, amino, carboxyl or saturated or unsaturated $C_{3-10}$ (carbocycle or heterocycle) optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy; and
  $C_{3-7}$ cycloalkyl fused to $C_{6-10}$ aryl optionally substituted with OH, halogen, amino, mercapto, carboxy, $C_{1-4}$ (alkyl, alkoxy, alkylthio, acyl, acyloxy or alkoxycarbonyl) optionally substituted with OH, halogen, amino or $C_{1-4}$ alkoxy;
$R_2$ and $R'_2$ are independently selected from H, or $C_{1-4}$ alkyl or $R_1$ and $R_2$ together form a saturated or unsaturated 5 or 6 member heterocycle optionally fused to $C_{6-10}$ aryl or heteroaryl;
$R_3$ and $R_4$ are independently selected from H, OH, halogen, amino, cyano, $C_{1-6}$ (alkyl, alkoxy, acyl, acyloxy or alkoxycarbonyl) optionally substituted with OH, halogen, amino or $C_{1-4}$ alkoxy, and saturated or unsaturated $C_{3-10}$ (carbocycle or heterocycle) optionally substituted with OH, halogen, amino, mercapto, $C_{1-4}$ alkylthio, $C_{1-4}$ alkoxycarbonyl, halo-substituted $C_{1-4}$ alkyl or halo-substituted $C_{1-4}$ alkoxy, $C_{1-4}$ alkyl, $C_{1-4}$ alkoxy or carboxy;

$R_5$ is H, $C_{1-6}$ alkyl or $C_{1-6}$ acyl optionally substituted with OH, halogen, amino or $C_{1-4}$ alkoxy; and n is 0, 1 or 2 wherein;

i) when A is

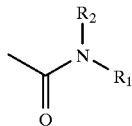

(II)

and when Y is N or $NR_5$, then $R_1$ is other than allyl or 2-methoxybenzyl; and (ii) when A is

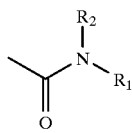

(II)

when Z is N or $NR_5$, then $R_1$ is other than methyl.

14. A compound according to claim 13, wherein Y is N or $NR_5$ and X and Z are independently selected from CH, $CR_4$, $CH_2$, C=O and $CHR_4$.

15. A compound according to claim 13, wherein $R_1$ is benzyl optionally substituted with one or two substituents selected from hydroxy, amino, halogen, $C_{1-4}$ alkyl, $C_{1-4}$ alkoxy, $C_{1-4}$ alkoxycarbonyl, $C_{1-4}$ alkylthio, $C_{1-4}$ halo-substituted alkyl.

16. A compound according to claim 15, wherein $R_2$, $R'_2$, R3 and $R_4$ are each H.

17. A compound selected from the group consisting of:
compound #1 N-(2-methylbenzyl)-2-(1,6) naphthyridinecarboxamide;
compound #2 N-benzyl-2-(1,6)naphthyridinecarboxamide;
compound #3 N-(4-bromobenzyl)-2-[1,6] naphthyridinecarboxamide
compound #4 N-(2-chlorobenzyl)-2-(1,6) naphthyridinecarboxamide;
compound #5 N-(2-bromobenzyl)-2-(1,6) naphthyridinecarboxamide;
compound #6 N-(3-bromobenzyl)-2-(1,6) naphthyridinecarboxamide;
compound #7 N-(2-fluorobenzyl)-2-(1,6) naphthyridinecarboxamide;
compound #8 N-(4-chlorobenzyl)-2-[1,6] naphthyridinecarboxamide;
compound #9 N-(2-ethyloxybenzyl)-2-(1,6) naphthyridinecarboxamide;
compound #10 [1,6]naphthyridine-2-carboxylic acid indan-1-ylamide
compound #11 [1,6]naphthyridine-2-carboxylic acid (1,2,3,4-tetrahydro-naphthalen-1-yl)-amide
compound #12 N-(3-methoxybenzyl)-2-(1,6) naphthyridinecarboxamide;
compound # 13 N-(2-trifluoromethylbenzyl)-2-(1,6) naphthyridinecarboxamide;
compound #14 N-(2,6-dimethoxybenzyl)-2-(1,6) naphthyridinecarboxamide;
compound #15 [1,6]naphthyridine-2-carboxylic acid (trans-2-phenylcyclopropyl)-amide
compound #16 N-(2-amino-6-fluorobenzyl)-2-[1,6] naphthyridinecarboxamide
compound #17 [1,6]naphthyridine-2-carboxylic acid (1-phenyl-ethyl) amide;
compound #18 [1,6]naphthyridine-2-carboxylic acid (pyridine-2-ylmethyl) amide
compound #19 [1,6]naphthyridine-2-carboxylic acid cyclohexylmethylamide
compound #20 (3,4-dihydro-1H-isoquinolin-2-yl)-[1,6] naphthyridin-2-yl-methanone
compound #21 N-(2-methylthiobenzyl)-2-[1,6] naphthyridine carboxamide
compound #22 N-(2-hydroxybenzyl)-2-(1,6)naphthyridine: carboxamide;
compound #23 N-(2-methoxycarbonylbenzyl)-2-(1,6) naphthyridinecarboxamide;
compound #26 N-(2propoxybenzyl)-2-[1,6]naphthyridine-2-carboxamide;
compound #27 (2-{[([1,6]naphthyridine-2-carbonyl)-amino]-methyl}phenyl)-carbonic acid tert-butyl ester;
compound #28 [1,6]Naphthyridine-2-carboxylic acid (2,3,4,5-tetrahydrobenzo[B]oxepin-5-yl)-amide;
compound #29 [1,6]Naphthyridine-2-carboxylic acid (chroman-4-yl)amide;
compound #30 N-(2'-methoxybenzyl)-5-amino-2[1,6] naphthyridinecarboxamide;
compound #31 [1,6]Naphthyridine-2-carboxylic acid 2,3-(methylenedioxy)-benzylamide;
compound #33 8-bromo-[1,6]naphthyridine-2-carboxylic acid (2-N-ethylaminobenzylamide);
compound #34 8-bromo-[1,6]naphthyridine-2-carboxylic acid (2-isopropoxybenzylamide);
compound #35 8-bromo-[1,6]naphthyridine-2-carboxylic acid (2-methoxybenzylamide);
compound #36 8-chloro-[1,6]naphthyridine-2-carboxylic acid (2-isopropoxybenzylamide);
compound #37 8-chloro-[1,6]naphthyridine-2-carboxylic acid (2-N-ethylaminobenzylamide);
compound #38 8-(2pyridyl)-[1,6]naphthyridine-2-carboxylic acid (2-isopropoxybenzylamide);
compound #39 [1,6]Naphthyridine-2-thiocarboxylic acid-2-trifluoromethylbenzylamide
compound #40 [1,6]Naphthyridine-2-thiocarboxylic acid-2-isopropoxybenzylamide;
compound #41 [1,6]Naphthyridine-2-thiocarboxylic acid-3-methoxybenzylamide;
compound #42 8-bromo-[1,6]Naphthyridine-2-thiocarboxylic acid-2-isopropoxybenzylamide;
compound #43 [1,6]Naphthyridine-2-thiocarboxylic acid 2-methoxybenzylamide;
compound #44 [1,6]Naphthyridine-2-thiocarboxylic acid 2-ethoxybenzylamide;
compound #45 [1,6]Naphthyridine-2-thiocarboxylic acid-2-methoxy-cyclohexylmethyl-amide;
compound #46 1-(2-iso-propoxy-phenyl)-3-[1,6] naphthyridin-2-yl-urea;
compound #47 1-(2-iso-propoxybenzyl)-3-[1,6] naphthyridin-2-yl-urea;
compound #48 1-(N-boc-4-aminobutyl)-3-[1,6] naphthyridin-2-yl-urea;
compound #49 1-(4-aminobutyl)-3-[1,6]-naphthyridin-2-yl-urea hydrochloride;

compound #50 1-[(S)-α-methylbenzyl]-3-[1,6]
naphthyridin-2-yl-urea;
compound #51 1-[(R)-α-methylbenzyl]-3-[1,6]
naphthyridin-2-yl-urea;
compound #52 1-(2-methoxy-phenyl)-3-[1,6]naphthyridin-2-yl-urea;
compound #53 1-butyl-3-[1,6]naphthyridin-2-yl-urea;
compound #54 1-(2-methoxybenzyl)-3-[1,6]naphthyridin-2-yl-urea;
compound #55 1-(2-ethoxy-phenyl)-3-[1,6]naphthyridin-2-yl-urea;
Compound #56 1-(2-methyl-phenyl)-3-[1,6]naphthyridin-2-yl-urea; and
Compound #57 8-(2-pyridyl)-[1,6]naphthyridine-2-carboxylic acid (2-isopropoxybenzylamide).

18. A compound selected from the group consisting of:
compound #2 N-benzyl-2-(1,6)naphthyridinecarboxamide;
compound #4 N-(2-chlorobenzyl)-2-(1,6)naphthyridinecarboxamide;
compound #12 N-(3-methoxybenzyl)-2-(1,6)naphthyridinecarboxamide;
compound #14 N-(2,6-dimethoxybenzyl)-2-(1,6)naphthyridinecarboxamide;
compound #19 [1,6]naphthyridine-2-carboxylic acid cyclohexylmethylamide
compound #26 N-(2propoxybenzyl)-2-[1,6]naphthyridine-2-carboxamide;
compound #28 [1,6]Naphthyridine-2-carboxylic acid (2,3,4,5-tetrahydrobenzo[B]oxepin-5-yl)-amide;
compound #31 [1,6]Naphthyridine-2-carboxylic acid 2,3-(methylenedioxy)-benzylamide;
compound #33 8-bromo-[1,6]naphthyridine-2-carboxylic acid (2-N-ethylaminobenzylamide);
compound #35 8-bromo-[1,6]naphthyridine-2-carboxylic acid (2-methoxybenzylamide);
compound #36 8-chloro-[1,6]naphthyridine-2-carboxylic acid (2-isopropoxybenzylamide);
compound #40 [1,6]Naphthyridine-2-thiocarboxylic acid-2-isopropoxybenzylamide;
compound #43 [1,6]Naphthyridine-2-thiocarboxylic acid 2-methoxybenzylamide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea; and
compound #51 1-[(R)-α-methylbenzyl]-3-[1,6]naphthyridin-2-yl-urea.

19. A compound selected from the group consisting of:
Compound #26 N-(2-propoxybenzyl)-2-[1,6]naphthyridine-2-carboxamide;
compound #33 8-bromo-[1,6]naphthyridine-2-carboxylic acid (2-N-ethylaminobenzylamide);
compound #36 8-chloro-[1,6]naphthyridine-2-carboxylic acid (2-isopropoxybenzylamide);
compound #40 [1,6]Naphthyridine-2-thiocarboxylic acid-2-isopropoxybenzylamide;
compound #43 [1,6]Naphthyridine-2-thiocarboxylic acid 2-methoxybenzylamide;
compound #46 1 -(2-iso-propoxy-phenyl)-3-[1,6]naphthyridin-2-yl-urea;
compound #47 1-(2-iso-propoxybenzyl)-3-[1,6]naphthyridin-2-yl-urea; and
compound #51 1-[(R)-(α-methylbenzyl]-3-[1,6]naphthyridin-2-yl-urea.

20. A compound selected from the group consisting of:
compound #26 N-(2propoxybenzyl)-2-[1,6]naphthyridine-2-carboxamide;

compound #32 7,8-dihydroisoquinolin-6-carboxylic acid 2'-methoxybenzylamide;
compound #33 8-bromo-[1,6]naphthyridine-2-carboxylic acid (2-N-ethylaminobenzylamide);
compound #40 [1,6]Naphthyridine-2-thiocarboxylic acid-2-isopropoxybenzylamide; and
compound #46 1-(2-iso-propoxy-phenyl)-3-[1,6]naphthyridin-2-yl-urea.

21. An anti-cytomegalovirus composition comprising a pharmaceutically acceptable carrier, diluent or adjunct, and a compound selected from the group consisting of:
compound #1 N-(2-methylbenzyl)-2(1,6)naphthyridinecarboxamide;
compound #2 N-benzyl-2-(1,6)naphthyridinecarboxamide;
compound #3 N-(4-bromobenzyl)-2-[1,6]naphthyridinecarboxamide
compound #4 N-(2-chlorobenzyl)-2-(1,6)naphthyridinecarboxamide;
compound #5 N-(2-bromobenzyl)-2-(1,6) naphthyridinecarboxamide;
compound #6 N-(3-bromobenzyl)-2-(1,6) naphthyridinecarboxamide;
compound #7 N-(2-fluorobenzyl)-2-(1,6)naphthyridinecarboxamide;
compound #8 N-(4-chlorobenzyl)-2-[1,6]naphthyridinecarboxamide;
compound #9 N-(2-ethyloxybenzyl)-2-(1,6)naphthyridinecarboxamide;
compound #10 [1,6]naphthyridine-2-carboxylic acid indan-1-ylamide
compound #11 [1,6]naphthyridine-2-carboxylic acid (1,2,3,4-tetrahydro-naphthalen-1-yl)-amide
compound #12 N-(3-methoxybenzyl)-2-(1,6)naphthyridinecarboxamide;
compound #13 N-(2-trifluoromethylbenzyl)-2-(1,6)naphthyridinecarboxamide;
compound #14 N-(2,6-dimethoxybenzyl)-2-(1,6)naphthyridinecarboxamide;
compound #15 [1,6]naphthyridine-2-carboxylic acid (trans-2-phenylcyclopropyl)-amide
compound #16 N-(2-amino-6-fluorobenzyl)-2[1,6]naphthyridinecarboxamide
compound #17 [1,6]naphthyridine-2-carboxylic acid (1-phenyl-ethyl) amide;
compound #18 [1,6]naphthyridine-2-carboxylic acid (pyridine-2-ylmethyl) amide
compound #19 [1,6]naphthyridine-2-carboxylic acid cyclohexylmethylamide
compound #20 (3,4-dihydro-1H-isoquinolin-2-yl)-[1,6]naphthyridin-2-yl-methanone
compound #21 N-(2-methylthiobenzyl)-2-[1,6]naphthyridin(carboxamide
compound #22 N-(2 -hydroxybenzyl)-2-(1,6) naphthyridinecarboxamide;
compound #23 N- (2-methoxycarbonylbenzyl)-2-(1,6) naphthyridinecarboxamide;
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;
compound #27 (2-{[([1,6]naphthyridine-2-carbonyl)-amino]-methyl}-phenyl)-carbonic acid tert-butyl ester;
compound #28 [1,6]Naphthyridine-2-carboxylic acid (2,3,4,5-tetrahydrobenzo[B]oxepin-5-yl)amide;
compound #29 [1,6]Naphthyridine-2-carboxylic acid (chroman-4-yl)amide;

compound #30 N-(2'-methoxybenzyl)-5-amino-2-[1,6]
naphthyridinecarboxamide;
compound #31 [1,6]Naphthyridine-2-carboxylic acid 2,3-
(methylenedioxy)-benzylamide;
compound #33 8-bromo-[1,6]naphthyridine-2-carboxylic
acid (2-N-ethylaminobenzylamide);
compound #34 8-bromo-[1,6]naphthyridine-2-carboxylic
acid (2-isopropoxybenzylamide);
compound #35 8-bromo-[1,6]naphthyridine-2-carboxylic
acid (2-methoxybenzylamide);
compound #36 8-chloro-[1,6]naphthyridine-2-carboxylic
acid (2-isopropoxybenzylamide);
compound #37 8-chloro-[1,6]naphthyridine-2-carboxylic
acid (2-N-ethylaminobenzylamide);
compound #38 8-(2pyridyl)-[1,6]naphthyridine-2-
carboxylic acid (2-isopropoxybenzylamide);
compound #39 [1,6]Naphthyridine-2-thiocarboxylic acid-2-
trifluoromethylbenzylamide
compound #40 [1,6]Naphthyridine-2-thiocarboxylic acid-2-
isopropoxybenzylamide;
compound #41 [1,6]Naphthyridine-2-thiocarboxylic acid-3-
methoxybenzylamide;
compound #42 8-bromo-[1,6]Naphthyridine-2-
thiocarboxylic acid-2-isopropoxybenzylamide;
compound #43 [1,6]Naphthyridine-2-thiocarboxylic acid
2-methoxybenzylamide;
compound #44 [1,6]Naphthyridine-2-thiocarboxylic acid
2-ethoxybenzylamide;
compound #45 [1,6]Naphthyridine-2-thiocarboxylic acid-2-
methoxy-cyclohexylmethyl-amide;
compound #46 1-(2-iso-propoxy-phenyl)-3-[1,6]
naphthyridin-2-yl-urea;
compound #47 1-(2-iso-propoxybenzyl)-3-[1,6]
naphthyridin-2-yl-urea;
compound #48 1-(N-boc-4-aminobutyl)-3-[1,6]
naphthyridin-2-yl-urea;
compound #49 1-(4-aminobutyl)-3-[1,6]naphthyridin-2-yl-
urea hydrochloride;
compound #50 1-[(S)-α-methylbenzyl]-3-[1,6]
naphthyridin-2-yl-urea;
compound #51 1-[(R)-α-methylbenzyl]-3-[1,6]
naphthyridin-2-yl-urea;
compound #52 1-(2-methoxy-phenyl)-3-[1,6]naphthyridin-
2-yl-urea;
compound #53 1-butyl-3-[1,6]naphthyridin-2-yl-urea;
compound #54 1-(2-methoxybenzyl)-3-[1,6]naphthyridin-2-
yl-urea;
compound #55 1-(2-ethoxy-phenyl)-3-[1,6]naphthyridin-2-
yl-urea;
Compound #56 1-(2-methyl-phenyl)-3-[1,6]naphthyridin-2-
yl-urea; and
Compound #57 8-(2-pyridyl)-[1,6]naphthyridine-2-
carboxylic acid (2-isopropoxybenzylamide).

22. An anti-cytomegalovirus composition comprising a
pharmaceutically acceptable carrier, diluent or adjunct, and
a compound selected from the group consisting of:
compound #2 N-benzyl-2-(1,6)naphthyridinecarboxamide;
compound #4 N-(2-chlorobenzyl)-2-(1,6)
naphthyridinecarboxamide;
compound #12 N-(3-methoxybenzyl)-2-(1,6)
naphthyridinecarboxamide;
compound #14 N-(2,6-dimethoxybenzyl)-2-(1,6)
naphthyridinecarboxamide;
compound #19 [1,6]naphthyridine-2-carboxylic acid cyclo-
hexylmethylamide
compound #24 (1,6)naphthyridine-2-carboxylic acid allyla-
mide (PFC-029);

compound #25 N-(2-methoxybenzyl)-2-(1,6)
naphthyridinecarboxamide;
compound #26 N-(2propoxybenzyl)-2-[1,6]naphthyridine-
2-carboxamide;
compound #28 [1,6]Naphthyridine-2-carboxylic acid (2,3,
4,5-tetrahydrobenzo[B]oxepin-5-yl)-amide;
compound #31 [1,6]Naphthyridine-2-carboxylic acid 2,3-
(methylenedioxy)-benzylamide;
compound #33 8-bromo-[1,6]naphthyridine-2-carboxylic
acid (2-N-ethylaminobenzylamide);
compound #35 8-bromo-[1,6]naphthyridine-2-carboxylic
acid (2-methoxybenzylamide);
compound #36 8-chloro-[1,6]naphthyridine-2-carboxylic
acid (2-isopropoxybenzylamide);
compound #40 [1,6]Naphthyridine-2-thiocarboxylic acid-2-
isopropoxybenzylamide;
compound #43 [1,6]Naphthyridine-2-thiocarboxylic acid
2-methoxybenzylamide;
compound #46 1-(2-iso-propoxy-phenyl)-3-[1,6]
naphthyridin-2-yl-urea;
compound #47 1-(2-iso-propoxybenzyl)-3-[1,6]
naphthyridin-2-yl-urea; and
compound #51 1-[(R)-α-methylbenzyl]-3-[1,6]
naphthyridin-2-yl-urea.

23. An anti-cytomegalovirus composition comprising a
pharmaceutically acceptable carrier, diluent or adjunct, and
a compound selected from the group consisting of:
Compound #26 N-(2-propoxybenzyl)-2-[1,6]naphthyridine-
2-carboxamide;
compound #33 8-bromo-[1,6]naphthyridine-2-carboxylic
acid (2-N-ethylaminobenzylamide);
compound #36 8-chloro-[1,6]naphthyridine-2-carboxylic
acid (2-isopropoxybenzylamide);
compound #40 [1,6]Naphthyridine-2-thiocarboxylic acid-2-
isopropoxybenzylamide;
compound #43 [1,6]Naphthyridine-2-thiocarboxylic acid
2-methoxybenzylamide;
compound #46 1-(2-iso-propoxy-phenyl)-3-[1,6]
naphthyridin -2-yl-urea;
compound #47 1-(2-iso-propoxybenzyl)-3-[1,6]
naphthyridin-2-yl-urea; and
compound #51 1-[(R)-α-methylbenzyl]-3-[1,6]
naphthyridin-2-yl-urea.

24. An anti-cytomegalovirus composition comprising a
pharmaceutically acceptable carrier, diluent or adjunct, and
a compound selected from the group consisting of:
compound #26 N-(2propoxybenzyl)-2-[1,6]naphthyridine-
2-carboxamide;
compound #32 7,8-dihydroisoquinolin-6-carboxylic acid
2'-methoxybenzylamide;
compound #33 8-bromo-[1,6]naphthyridine-2-carboxylic
acid (2-N-ethylaminobenzylamide);
compound #40 [1,6]Naphthyridine-2-thiocarboxylic acid-2-
isopropoxybenzylamide; and
compound #46 1-(2-iso-propoxy-phenyl)-3-[1,6]
naphthyridin-2-yl-urea.

25. A method of inhibiting cytomegalovirus replication in
a mammal, comprising administering to said mammal an
anti-cytomegalovirus amount of a compound selected from
the group consisting of:
compound #1 N-(2-methylbenzyl)-2-(1,6)
naphthyridinecarboxamide;
compound #2 N-benzyl-2-(1,6)naphthyridinecarboxamide;
compound #3 N-(4-bromobenzyl)-2-[1,6]naphthyridine-
carboxamide
compound #4 N-(2-chlorobenzyl)-2-(1,6)
naphthyridinecarboxamide;

compound #5 N-(2-bromobenzyl)-2-(1,6)naphthyridinecarboxamide;
compound #6 N-(3-bromobenzyl)-2-(1,6)naphthyridinecarboxamide;
compound #7 N-(2-fluorobenzyl)-2-(1,6)naphthyridinecarboxamide;
compound #8 N-(4-chlorobenzyl)-2-[1,6]naphthyridinecarboxamide;
compound #9 N-(2-ethyloxybenzyl)-2-(1,6)naphthyridinecarboxamide;
compound #10 [1,6]naphthyridine-2-carboxylic acid indan-1-ylamide
compound #11 [1,6]naphthyridine-2-carboxylic acid (1,2,3,4-tetrahydro-naphthalen-1-yl)-amide
compound #12 N-(3-methoxybenzyl)-2-(1,6)naphthyridinecarboxamide;
compound #13 N-(2-trifluoromethylbenzyl)-2-(1,6)naphthyridinecarboxamide;
compound # 14 N-(2,6-dimethoxybenzyl)-2-(1,6)naphthyridinecarboxamide;
compound #15 [1,6]naphthyridine-2-carboxylic acid (trans-2-phenylcyclopropyl)-amide
compound # 16 N-(2-amino-6-fluorobenzyl)-2[1,6]naphthyridinecarboxamide
compound #17 [1,6]naphthyridine-2-carboxylic acid (1-phenyl-ethyl) amide;
compound #18 [1,6]naphthyridine-2-carboxylic acid (pyridine-2-ylmethyl) amide
compound #19 [1,6]naphthyridine-2-carboxylic acid cyclohexylmethylamide
compound #20 (3,4-dihydro-1h-isoquinolin-2-yl)-[1,6]naphthyridin-2-yl-methanone
compound #21 N-(2-methylthiobenzyl)-2-[1,6]naphthyridine carboxamide
compound #22 N-(2-hydroxybenzyl)-2-(1,6)naphthyridinecarboxamide;
compound #23 N-(2-methoxycarbonylbenzyl)-2-(1,6)naphthyridinecarboxamide;
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;
compound #27 (2-{[([1,6]naphthyridine-2-carbonyl)-amino]-methyl}phenyl)-carbonic acid tert-butyl ester;
compound #28 [1,6]Naphthyridine-2-carboxylic acid (2,3,4,5-tetrahydrobenzo[B]oxepin-5-yl)-amide;
compound #29 [1,6]Naphthyridine-2-carboxylic acid (chroman-4-yl)-amide;
compound #30 N-(2'-methoxybenzyl)-5-amino-2-[1,6]naphthyridinecarboxamide;
compound #31 [1,6]Naphthyridine-2-carboxylic acid 2,3-(methylenedioxy)-benzylamide;
compound #33 8-bromo-[1,6]naphthyridine-2-carboxylic acid (2-N-ethylaminobenzylamide);
compound #34 8-bromo-[1,6]naphthyridine-2-carboxylic acid (2-isopropoxybenzylamide);
compound #35 8-bromo-[1,6]naphthyridine-2-carboxylic acid (2-methoxybenzylamide);
compound #36 8-chloro-[1,6]naphthyridine-2-carboxylic acid (2-isopropoxybenzylamide);
compound #37 8-chloro-[1,6]naphthyridine-2-carboxylic acid (2-N-ethylaminobenzylamide);
compound #38 8-(2pyridyl)-[1,6]naphthyridine-2-carboxylic acid (2-isopropoxybenzylamide);
compound #39 [1,6]Naphthyridine-2-thiocarboxylic acid-2-trifluoromethylbenzylamide
compound #40 [1,6]Naphthyridine-2-thiocarboxylic acid-2-isopropoxybenzylamide;
compound #41 [1,6]Naphthyridine-2-thiocarboxylic acid-3-methoxybenzylamide;
compound #42 8-bromo-[1,6]Naphthyridine-2-thiocarboxylic acid-2-isopropoxybenzylamide;
compound #43 [1,6]Naphthyridine-2-thiocarboxylic acid 2-methoxybenzylamide;
compound #44 [1,6]Naphthyridine-2-thiocarboxylic acid 2-ethoxybenzylamide;
compound #45 [1,6]Naphthyridine-2-thiocarboxylic acid-2-methoxy-cyclohexylmethyl-amide;
compound #46 1-(2-iso-propoxy-phenyl)-3-[1,6]naphthyridin-2-yl-urea;
compound #47 1-(2-iso-propoxybenzyl)-3-[1,6]naphthyridin-2-yl-urea;
compound #48 1-(N-boc-4-aminobutyl)-3-[1,6]naphthyridin-2 -yl-urea;
compound #49 1-(4-aminobutyl)-3-[1,6]naphthyridin-2 -yl-urea hydrochloride;
compound #50 1-[(S)-α-methylbenzyl]-3-[1,6]naphthyridin-2-yl-urea;
compound #51 1-[(R)-α-methylbenzyl]-3-[1,6]naphthyridin-2-yl-urea;
compound #52 1-(2-methoxy-phenyl)-3-[1,6]naphthyridin-2-yl-urea;
compound #53 1-butyl-3-[1,6]naphthyridin-2-yl-urea;
compound #54 1-(2-methoxybenzyl)-3-[1,6]naphthyridin-2-yl-urea;
compound #55 1-(2-ethoxy-phenyl)-3-[1,6]naphthyridin-2-yl-urea;
Compound #56 1-(2-methyl-phenyl)-3-[1,6]naphthyridin-2-yl-urea; and
Compound #57 8-(2-pyridyl)-[1,6]naphthyridine-2-carboxylic acid (2-isopropoxybenzylamide).

26. A method of inhibiting cytomegalovirus replication in a mammal, comprising administering to said mammal an anti-cytomegalovirus amount of a compound selected from the group consisting of:
compound #2 N-benzyl-2-(1,6)naphthyridinecarboxamide;
compound #4 N-(2 -chlorobenzyl)-2-(1,6)naphthyridinecarboxamide;
compound # 12 N-(3-methoxybenzyl)-2-(1,6)naphthyridinecarboxamide;
compound #14 N-(2,6-dimethoxybenzyl)-2-(1,6)naphthyridinecarboxamide;
compound #19 [1,6]naphthyridine-2-carboxylic acid cyclohexylmethylamide
compound #24 (1,6)naphthyridine-2-carboxylic acid allylamide (PFC-029);
compound #25 N-(2-methoxybenzyl)-2-(1,6)naphthyridinecarboxamide;
compound #26 N-(2propoxybenzyl)-2-[1,6]naphthyridine-2-carboxamide;
compound #28 [1,6]Naphthyridine-2-carboxylic acid (2,3,4,5-tetrahydrobenzo[B]oxepin-5-yl)-amide;
compound #31 [1,6]Naphthyridine-2-carboxylic acid 2,3-(methylenedioxy)-benzylamide;
compound #33 8-bromo-[1,6]naphthyridine-2-carboxylic acid (2-N-ethylaminobenzylamide);
compound #35 8-bromo-[1,6]naphthyridine-2-carboxylic acid (2-methoxybenzylamide);
compound #36 8-chloro-[1,6]naphthyridine-2-carboxylic acid (2-isopropoxybenzylamide);
compound #40 [1,6]Naphthyridine-2-thiocarboxylic acid-2-isopropoxybenzylamide;
compound #43 [1,6]Naphthyridine-2-thiocarboxylic acid 2-methoxybenzylamide;

compound #46 1-(2-iso-propoxy-phenyl)-3-[1,6]
naphthyridin-2-yl-urea;
compound #47 1 -(2-iso-propoxybenzyl)-3-[1,6]
naphthyridin- 2-yl-urea; and
compound #51 1-[(R)-α-methylbenzyl]-3-[1,6]
naphthyridin-2 -yl-urea.

27. A method of inhibiting cytomegalovirus replication in a mammal, comprising administering to said mammal an anti-cytomegalovirus amount of a compound selected from the group consisting of:

Compound #26 N-(2-propoxybenzyl)-2-[1,6]naphthyridine-2-carboxamide;
compound #33 8-bromo-[1,6]naphthyridine-2-carboxylic acid (2-N-ethylaminobenzylamide);
compound #36 8-chloro-[1,6]naphthyridine-2-carboxylic acid (2-isopropoxybenzylamide);
compound #40 [1,6]Naphthyridine-2-thiocarboxylic acid-2-isopropoxybenzylamide;
compound #43 [1,6]Naphthyridine-2-thiocarboxylic acid 2-methoxybenzylamide;
compound #46 1-(2-iso-propoxy-phenyl)-3-[1,6] naphthyridin-2-yl-urea;
compound #47 1-(2-iso-propoxybenzyl)-3-[1,6] naphthyridin-2-yl-urea; and
compound #51 1-[(R)-α-methylbenzyl]-3-[1,6] naphthyridin-4-yl-urea.

28. A method of inhibiting cytomegalovirus replication in a mammal, comprising administering to said mammal an anti-cytomegalovirus amount of a compound selected from the group consisting of:

compound #26 N-(2propoxybenzyl)-2-[1,6]naphthyridine-2-carboxamide;
compound #32 7,8-dihydroisoquinolin-6-carboxylic acid 2'-methoxybenzylamide;
compound #33 8-bromo-[1,6]naphthyridine-2-carboxylic acid (2-N-ethylaminobenzylamide);
compound #40 [1,6]Naphthyridine-2-thiocarboxylic acid-2-isopropoxybenzylamide; and
compound #46 1-(2-iso-propoxy-phenyl)-3-[1,6] naphthyridin-2-yl-urea.

* * * * *